United States Patent [19]
Vo-Dinh

[11] Patent Number: 5,938,617
[45] Date of Patent: *Aug. 17, 1999

[54] ADVANCED SYNCHRONOUS LUMINESCENCE SYSTEM FOR THE DETECTION OF BIOLOGICAL AGENTS AND INFECTIOUS PATHOGENS

[75] Inventor: Tuan Vo-Dinh, Knoxville, Tenn.

[73] Assignee: Lockhead Martin Energy Research Corporation, Oak Ridge, Tenn.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/760,165

[22] Filed: Dec. 3, 1996

Related U.S. Application Data

[63] Continuation-in-part of application No. 08/300,202, Sep. 2, 1994, Pat. No. 5,599,717.

[51] Int. Cl.$^6$ ...................................................... A61B 6/00
[52] U.S. Cl. ........................ 600/476; 600/477; 600/478; 436/20; 436/63; 436/171; 436/172
[58] Field of Search ................................ 600/473, 475, 600/476–478, 310, 314, 342; 436/63, 64, 171, 172, 20–24

[56] References Cited

U.S. PATENT DOCUMENTS

| | | |
|---|---|---|
| 4,930,516 | 6/1990 | Alfano et al. . |
| 5,042,494 | 8/1991 | Alfano . |
| 5,131,398 | 7/1992 | Alfano et al. . |
| 5,261,410 | 11/1993 | Alfano et al. . |
| 5,272,089 | 12/1993 | Vo-Dinh . |
| 5,293,872 | 3/1994 | Alfano et al. ............................ 600/475 |
| 5,303,026 | 4/1994 | Strobl et al. . |
| 5,306,403 | 4/1994 | Vo-Dinh . |
| 5,318,751 | 6/1994 | Vo-Dinh . |
| 5,377,003 | 12/1994 | Lewis et al. ............................ 356/300 |
| 5,599,717 | 2/1997 | Vo-Dinh ................................... 436/63 |

OTHER PUBLICATIONS

*Autofluorescence of Normal and Malignant Bronchial Tissue*, by Jaclyn Hung MSc, Stephen Lam, MD, Jean C. LeRiche, MBChB, and Banko Palcic, PhD (Lasers in Surgery and Medicine 11:99–105 (1991).

*Multicomponent Analysis by Synchronous Luminescence Spectrometry*, by Tuan Vo–Dinh (Reprinted from Analytical Chemistry, vol. 50, p. 396, Mar. 1978).

*Synchronous Excitation Spectroscopy*, by T. Vo–Dinh (From: Modern Fluorescence Spectroscopy vol. 4; Plenum Publishing Corp., 1981).

Rao, C.M. "Synchronous Scan Fluorescence Spectroscopy of Proteins and Human Eye Lenses" Biochemical and Biophysical Research Communications. vol. 176, No. 3 (1991) pp. 1351–1357, May 15, 1991.

Manchester, D.K. et al. "Detection of benzo(a)pyrene diol epoxide–DNA adducts in human placenta" Proc. Nat. Acad. Sci. USA, vol. 85 (1988) pp. 9243–9247.

Rubio, S. et al. "Analytical Applications of Synchronous Fluorescence Spectroscopy" Talanta, vol. 33. No. 8 (1986) pp. 633–640.

*Primary Examiner*—Ruth S. Smith
*Attorney, Agent, or Firm*—Quales & Brady LLP

[57] ABSTRACT

A method and apparatus for detecting and identifying biological pathogens in a sample includes exposing the sample to an excitation radiation and thereby generating an emission radiation, synchronously scanning the wavelength of the excitation radiation and the wavelength of the emission radiation to produce a spectrum, and correlating the spectrum to a biological pathogen in the sample. In another aspect, a method and apparatus for imaging chemical and biological agents in a sample includes exposing the sample to an excitation radiation and thereby generating an emission radiation and synchronously imaging the wavelength of the excitation radiation and the wavelength of the emission radiation to produce an imaged spectrum.

52 Claims, 18 Drawing Sheets

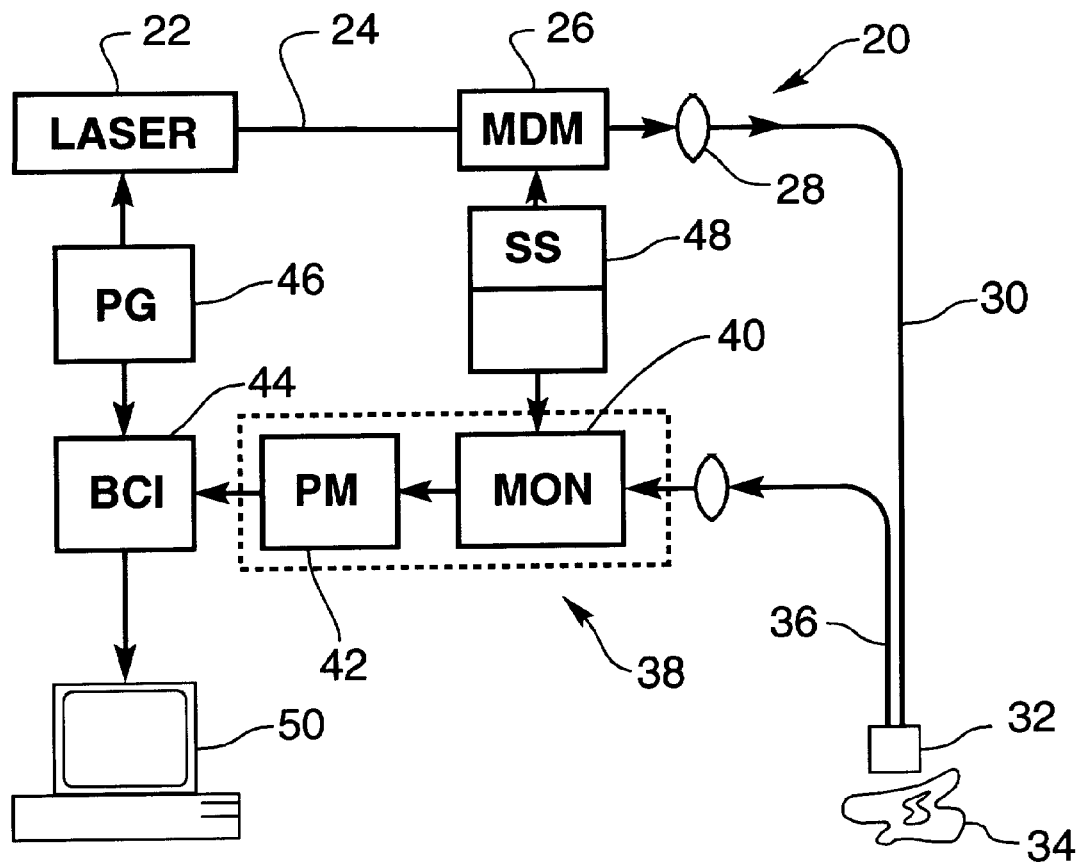
Fig. 2
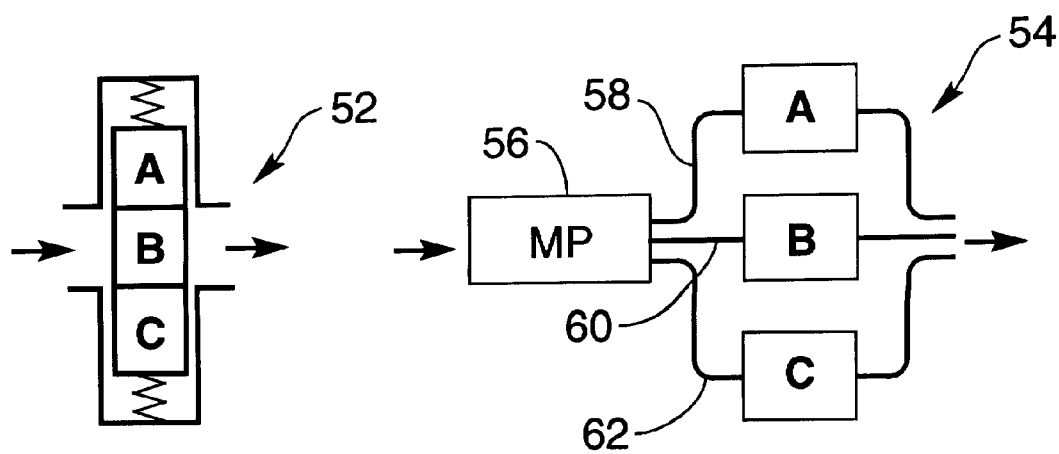
Fig. 3 Fig. 4

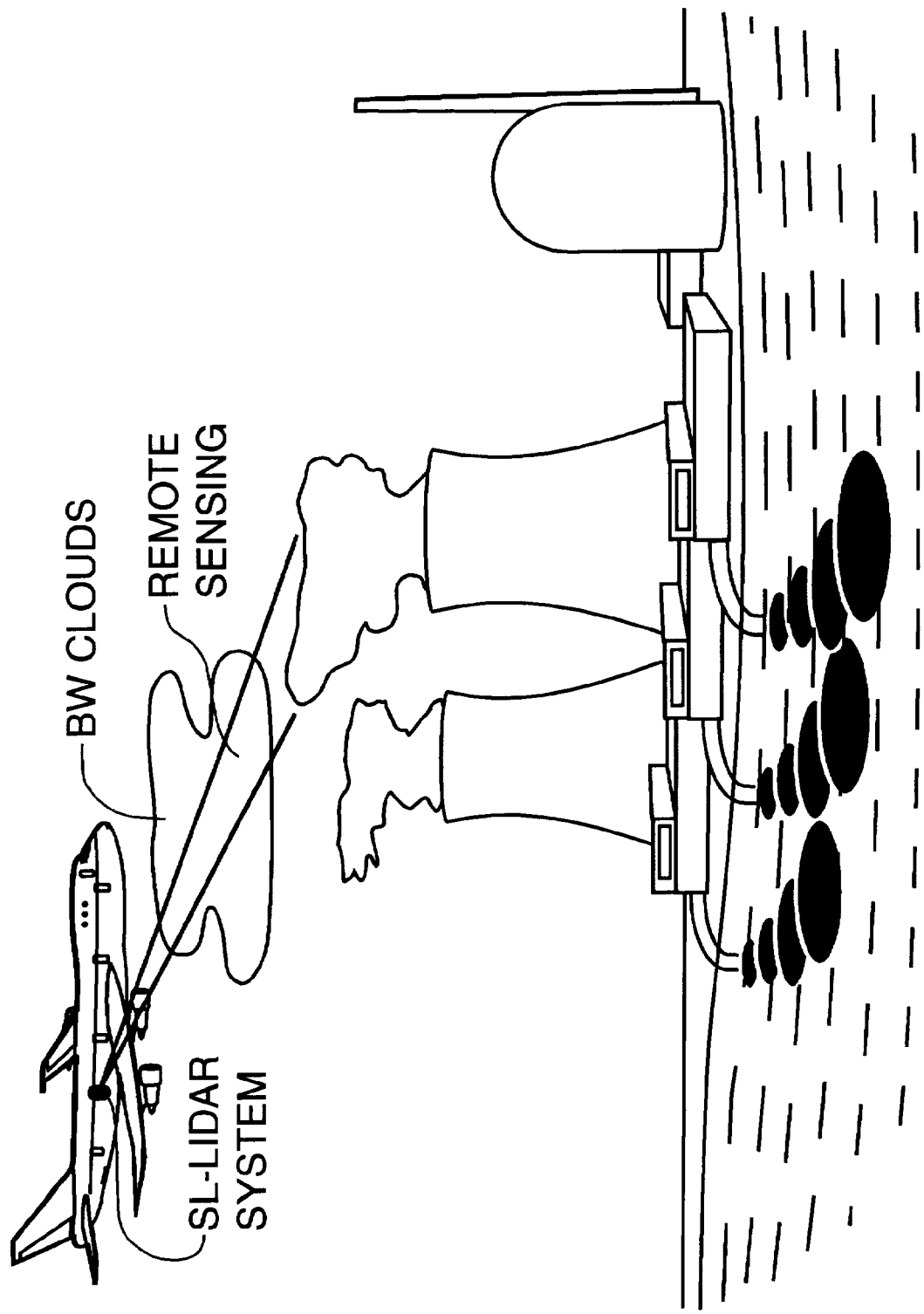

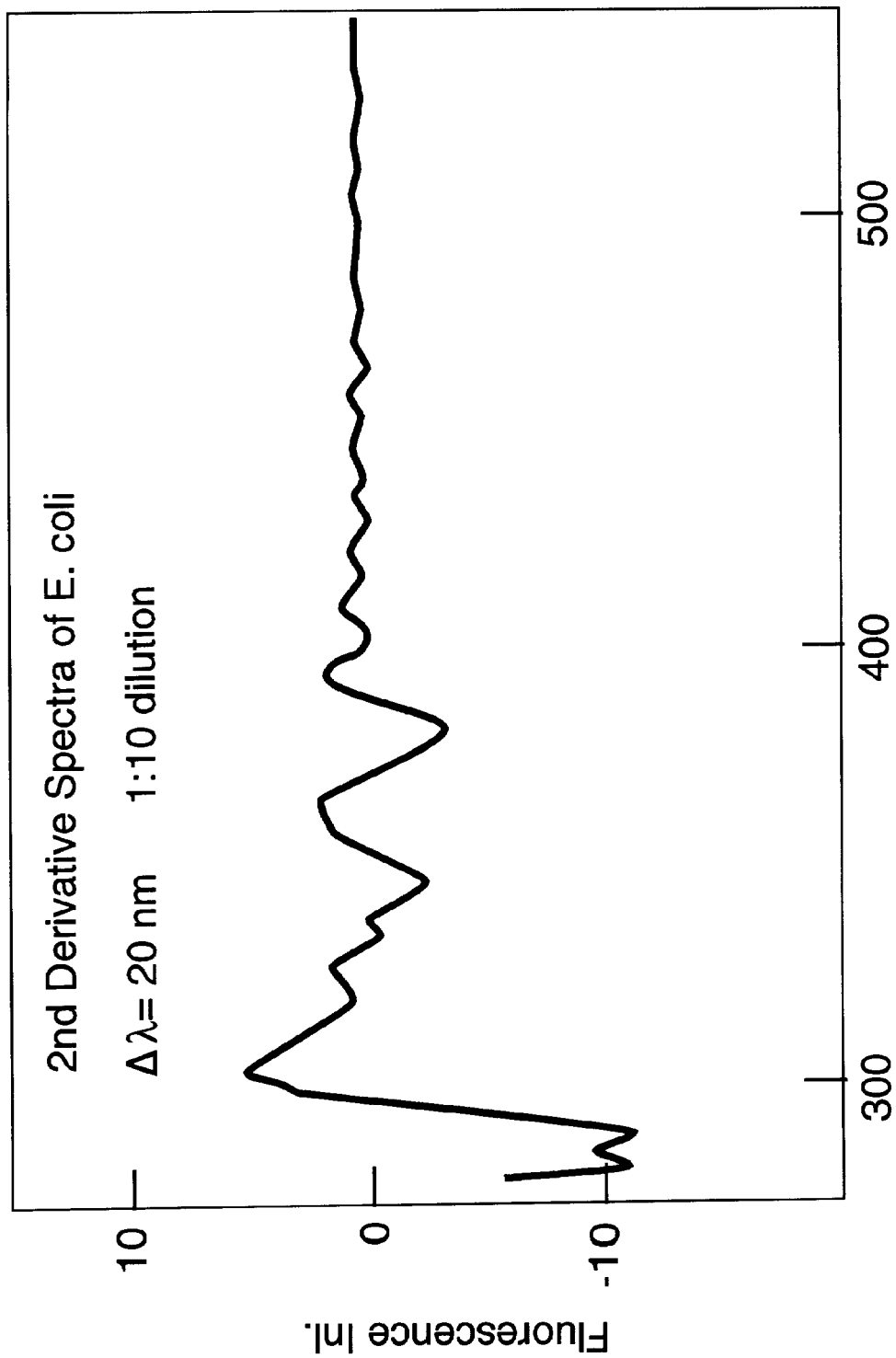

ADVANCED SYNCHRONOUS LUMINESCENCE SYSTEM FOR THE DETECTION OF BIOLOGICAL AGENTS AND INFECTIOUS PATHOGENS

This application is a continuation-in-part of copending U.S. patent application Ser. No. 08/300,202, filed Sep. 2, 1994, now U.S. Pat. No. 5,599,717.

This invention was made with Government support under contract DE-AC05-84OR21400 awarded by the U.S. Department of Energy to Martin Marietta Energy Systems, Inc. and the Government has certain rights in this invention.

FIELD OF THE INVENTION

The present invention relates generally to the fields of chemical analysis and biomedical diagnostics, and more specifically, to the use of synchronous luminescence to perform biomedical diagnostics and to screen for biological pathogens, including infectious agents, for example, infectious pathogens. A multi-dye laser source, or a light source coupled to one or more acousto-optic tunable filters is used to induce from a sample luminescence having a unique spectral signature.

BACKGROUND OF THE INVENTION

Laser-induced fluorescence (LIF) has been investigated recently as a method to discriminate tumors from normal tissues. LIF techniques have also been used to characterize pre-malignant colorectal lesions and to distinguish adenomatous polyps from normal colon tissue and hyperplastic polyps.

Others have investigated the use of LIF to distinguish adenomatous tissue from normal colon tissue in vivo. In these investigations, a laser such as a pulsed nitrogen laser-pumped dye laser system (370 nm) was used as the excitation source. The sensitivity, specificity and predictive value for diagnostics of their technique towards adenomas were reported to be very good. Because only a small number of hyperplastic polyps were examined, it is unclear whether colonic neoplasia can be reliably identified, since it is not known whether the observed differences in fluorescence arise from compositional changes specific to dysplasia or simply from structural differences between polyps and the colon.

The LIF technique has also been used to distinguish adenomatous from normal colon tissue in vitro. In a study conducted by Kapalia et al. in 1990, endoscopically resected polyps were excited using a continuous wave (cw) helium-cadmium laser (325 nm) and the resulting fluorescence of these endoscopically resected polyps was measured with an optical multichannel-analyzer system. They found that adenomatous polyps (51 of 51) could be reliably distinguished from normal colonic tissue (69 of 69) in vitro based on LIF scores from a stepwise multivariate linear regression (MVLR) analysis of their data. In addition, 15 of 16 hyperplastic polyps fell within the normal colonic tissue range, resulting in the ability to distinguish colonic neoplasia of resected tissue.

Schomacker et al., in 1992, also used a MVLR analysis method to distinguish neoplastic tissue from non-neoplastic tissue. Their data suggested that the LIF measurements sense changes in polyp morphology rather than changes in fluorplores specific to polyps, and it was this change in morphology that leads indirectly to discrimination of polyps. Schomacker concluded that the feasibility of discriminating groups of normal from dysplastic cells by LIF had not yet been demonstrated.

The above examples underscore the fact that, in spite of some specific successes, one of the major limitations of the LIF technique is its specificity. The laser used as the excitation source employed under current conditions can yield high intensity but does not provide a selective tool for excitation.

Tissue fluorescence is a complex process arising from the superposition of the fluorescence of many chemical species in tissue. Although changes in fluorescence profiles have been reported by many researchers involved, these changes are often difficult to provide unique "spectral signatures" useful for unequivocal diagnostic purposes.

In addition to spectral specificity problems, current instrumentation for cancer diagnostics have serious limitations. This limitation also applies to other uses, such as detection of geological species in air, water and soil samples, and screening food products for infectious pathogens. A laser-based LIF instrument can use only fixed excitation whereas conventional spectrometers (non-laser devices) do not provide rapid synchronous luminescence (SL) scanning capabilities for useful clinical applications.

Application of SL techniques to the detection of malignant tissue is described in a related application, Ser. No. 08/300,202, entitled "Advanced Synchronous Luminescence System." However, the application of synchronous luminescence to detection of biological pathogens in environmental and biological samples, or food products has not been described.

There is, therefore, a strong need to develop new or improved methods and instrumentation for sensitive as well as selective chemical analysis and biomedical diagnostics, particularly as applied to detection of biological pathogens, including infectious agents, for example, infectious pathogens.

SUMMARY OF THE INVENTION

An object of the present invention is to provide a method and apparatus which utilizes synchronous luminescence to identify biological pathogens.

Another object of the present invention is to provide a method and apparatus capable of making chemical identifications and/or medical diagnoses with relative speed, improved accuracy and efficiency, thereby leading to significant advances in the understanding of disease therapy in general and the effective detection of diseases caused by biological pathogens, such as viruses and bacteria.

Another object of the present invention is to provide a method and apparatus capable of rapidly detecting pathogenic agents in food products (e.g., processed meat, etc.), thereby improving public health safety.

Yet another object of this invention is to provide a method and apparatus capable of point-source and stand-off detection of biological agents in environmental samples.

These and other objects of the invention are met by providing a method of testing a sample which includes the steps of exposing the sample to an excitation radiation and thereby generating an emission radiation, synchronously scanning the wavelength of the excitation radiation and the wavelength of the emission radiation to produce a spectrum, and correlating the spectrum to that of a biological pathogen in the sample.

Another aspect of the present invention provides a method of imaging a sample which includes the steps of exposing the sample to an excitation radiation and thereby generating an emission radiation and synchronously scanning the wavelength of the excitation radiation and the wavelength of the emission radiation to produce a multi-spectral image.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

FIG. 2 is a schematic view of a first preferred embodiment of an instrument capable of making chemical and biomedical identifications according to the present invention;

FIG. 3 is a schematic view of a laser dye unit capable of use in the instrument of FIG. 2;

FIG. 4 is a schematic view of an alternative laser dye unit;

FIG. 15b is a more detailed schematic view of the SL-LIDAR system of FIG. 15a.

FIG. 15c is a schematic view of an example of how the SL-LIDAR system is used.

FIG. 19 is a display showing a second derivative spectrum of the synchronous luminescence spectrum of E. Coli bacteria.

DETAILED DESCRIPTION OF THE PREFERRED EMBODIMENT

The present invention combines the high intensity of a laser at the excitation source with the improved selectivity of the synchronous luminescence (SL) technique to perform chemical and biomedical diagnostics. The general theory of the SL method has been described previously in "Synchronous Excitation Spectroscopy," by T. Vo-Dinh, Modern Fluorescence Spectroscopy, Chapter 5, Ed. by E. L. Wehry (Plenum Publ. Corp. 1981), which is incorporated herein by reference.

Figure 1:
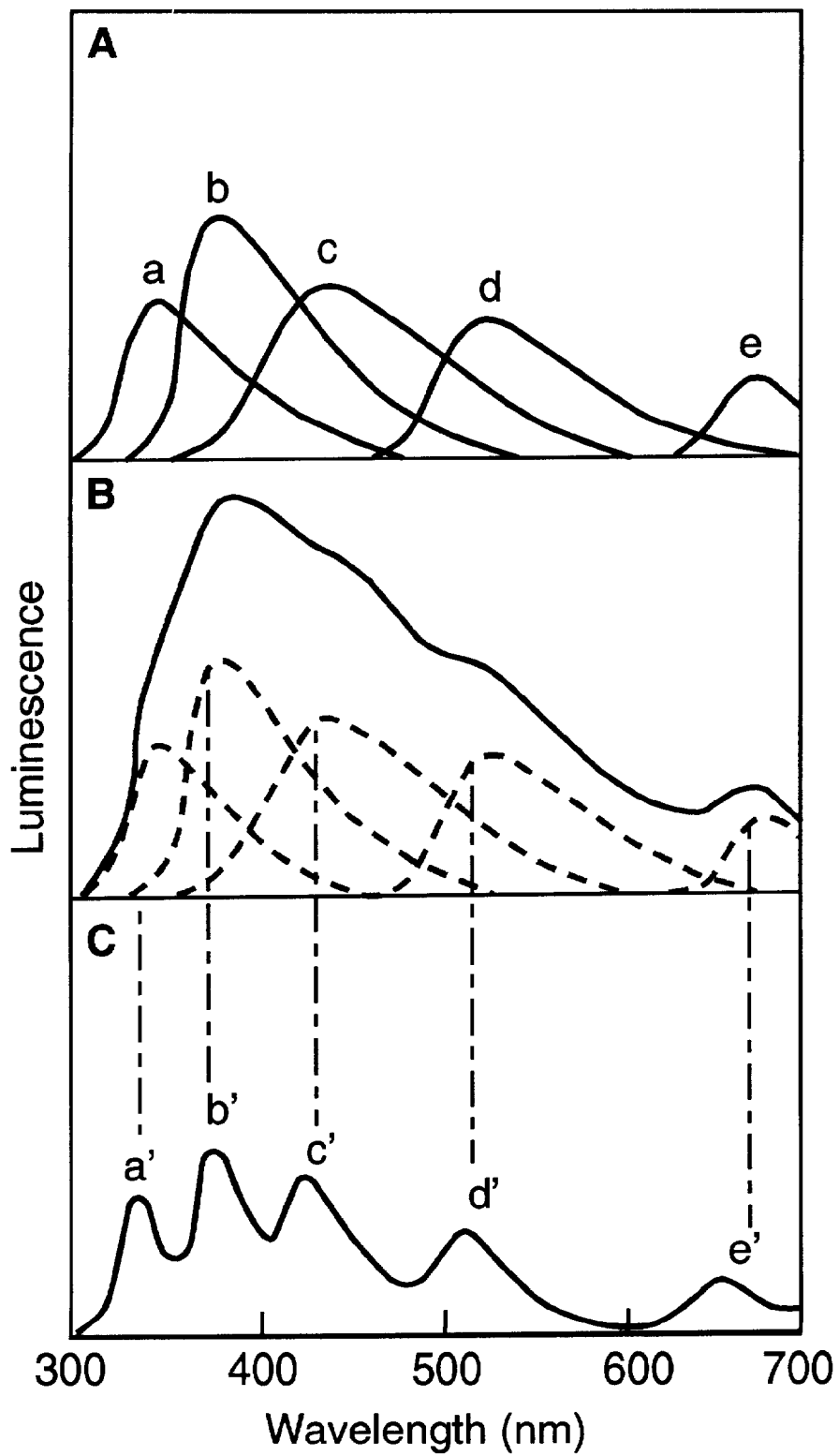
FIG. 1 is a composite graph showing fluorescence spectra of individual components of tissue, using conventional (i.e., fixed excitation) laser-induced fluorescence and using laser-induced synchronous luminescence of the present invention.

The principle of the synchronous luminescence approach for diagnostics of normal and cancer tissues is illustrated in FIG. 1. One of the problems of fluorescence technique as it is used currently is the fixed wavelength excitation source (e.g., a laser).

Fluorescence from tissues originate from many biological components (e.g., NADH, prophyrins, etc.). Each component has specific absorption and emission spectra occurring at determined spectral ranges, as seen in section "A" of FIG. 1. The spectra illustrated in A are as follows:

a=tryptophan
b=collagen
c=NADH
d=FAD
e=porphyrin

Thus, each curve of A represents the fluorescence of individual components in tissues which might be sampled for the presence of an abnormality, such as a malignancy. ("NADH" stands for nicotinamide adenine dinucleotide, and "FAD" stands for Flavin adenine dinucleotide)

In conventional laser-induced fluorescence (LIF), the laser excitation emission line is fixed (e.g., 337 nm for the nitrogen laser; 325 nm for the helium-cadmium laser). When a fixed laser line is used it is difficult, if not impossible, to excite all the biological components under optimal conditions. Another important limitation of conventional LIF is due to the fact that the fluorescence from tissues arises from the emission of different species, resulting in spectra that are poorly resolved and featureless because of spectral overlap between the emissions from individual components, as seen in the "B" section of FIG. 1. The laser used in LIF can only improve the sensitivity but does not enhance the selectivity.

With the present synchronous luminescence technique, both $\lambda_{em}$ and $\lambda_{ex}$ are scanned synchronously with a constant interval between the two wavelengths ($\Delta\lambda = \lambda_{em} - \lambda_{ex}$). Since the synchronous luminescence spectrum of each component becomes sharper due to the band-narrowing effect of the synchronous luminescence technique, the resulting fluorescence spectrum of the tissues sampled becomes more resolved with sharp peaks that are readily identified. These can be seen in section "C" of FIG. 1 as peaks a', b', c', d', and e'.

The present use of laser-induced synchronous luminescence (LISL) can provide a better spectral signature of tumors and normal tissues. Many subtle spectral features that are indiscernible in conventional LIF spectra can be revealed in the present LISL technique.

The laser used as the excitation source can yield high intensity but does not provide a selective tool for excitation. The observed fluorescence arises from the superposition of the fluorescence of many biochemical components in living systems. Although changes in fluorescence profiles have been observed, these changes are often difficult to provide "unique spectral signatures" useful for unequivocal identification of the pathogens. For example, the characterization of various types of pathogens using fixed-excitation LIF is difficult.

An instrument 20 capable of effecting LISL technique is shown schematically in FIG. 2. The instrument includes a laser 22 outputting a beam 24 having a given wavelength. The laser 20 could be a portable pulsed nitrogen laser, for example.

The output beam 24 is coupled to means 26 for changing the wavelength of the output beam 24. In the illustrated embodiment of FIG. 2, the means is a multi-dye module (MDM) 26. The output of the MDM 26 is delivered, through a focusing lens 28, to an optical fiber (or fibers) 30. The optical fiber 30 can be a single fiber of, for example, 600-$\mu$m diameter quartz optical fiber, or multi-fiber bundle could be employed. This fiber or fibers transmits the excitation radiation to the sample being investigated.

The optical fiber 30 transmits the output beam to a probe 32 juxtaposed a sample 34. The probe 32 can be inserted into the working channels of an endoscope for in vivo measurements.

An optical fiber (or fibers) 36 transmits the fluorescence of the sample 34 to detector means 38. The detector means 38 includes a monochromator (MON) 40 and a photomultiplier (PM) 42. A boxcar integrator (BCI) 44, synchronized with the laser pulse via a pulse generator (PG) 46 acting as a trigger is used to record and process the fluorescence signal. A synchronous scanning device (SS) 48 ensures that the excitation radiation ($\lambda_{ex}$) and the emission radiation ($\lambda_{em}$) are maintained at a constant interval ($\Delta\lambda$). A portable computer 50, or other suitable data collection, analysis and/or display devices, can be used to generate the synchronous luminescence spectra such as that which is illustrated in the C section of FIG. 1.

Testing can also be performed to confirm the presence of certain chemicals in the sample 34. In one experiment, a prototype of the instrument 20 was able to detect 680 zeptomoles ($10^{-21}$ moles) of tetracene.

A diagnosis of the sample 34 can be made by comparing the spectra of the sample to spectra for healthy tissue samples, for example. Further programming of the computer 50 could render comparison and diagnoses automatic by computer-assisted comparison of test spectra to pre-recorded or baseline spectra.

The MDM 26 can be any device capable of producing a suitable range of wavelengths for the scanning of $\lambda_{ex}$. One example is shown in FIG. 3, wherein a laser dye unit 52 includes three dye cells A, B and C, each containing a dye capable of producing a range of excitation wavelengths. For example, if the laser source is a nitrogen pump laser of 337 nm, the dye in cell A could be chosen to produce a range of wavelengths from 350–390 nm. The dye in cell B could be chosen to produce a 390–420 nm range, and the dye in cell C could be chosen to produce a 420–450 nm range. The dye cells are mounted in a quartz cuvette, through which the pump laser output passes. Springs on opposite sides of the dye cells help position the cells in the optical path of the pump laser. A motor of the synchronous scanning system 48 changes the dye cells and adjusts the grating of the dye system according to the desired scanning program.

An alternative embodiment of a laser dye unit 54 is shown in FIG. 4. The unit 54 includes a fiber optic multiplexer (MP) 56 which delivers the pump laser output to one of the three dye cells A, B, and C through respective optical fibers 58, 60 and 62.

Figure 5:
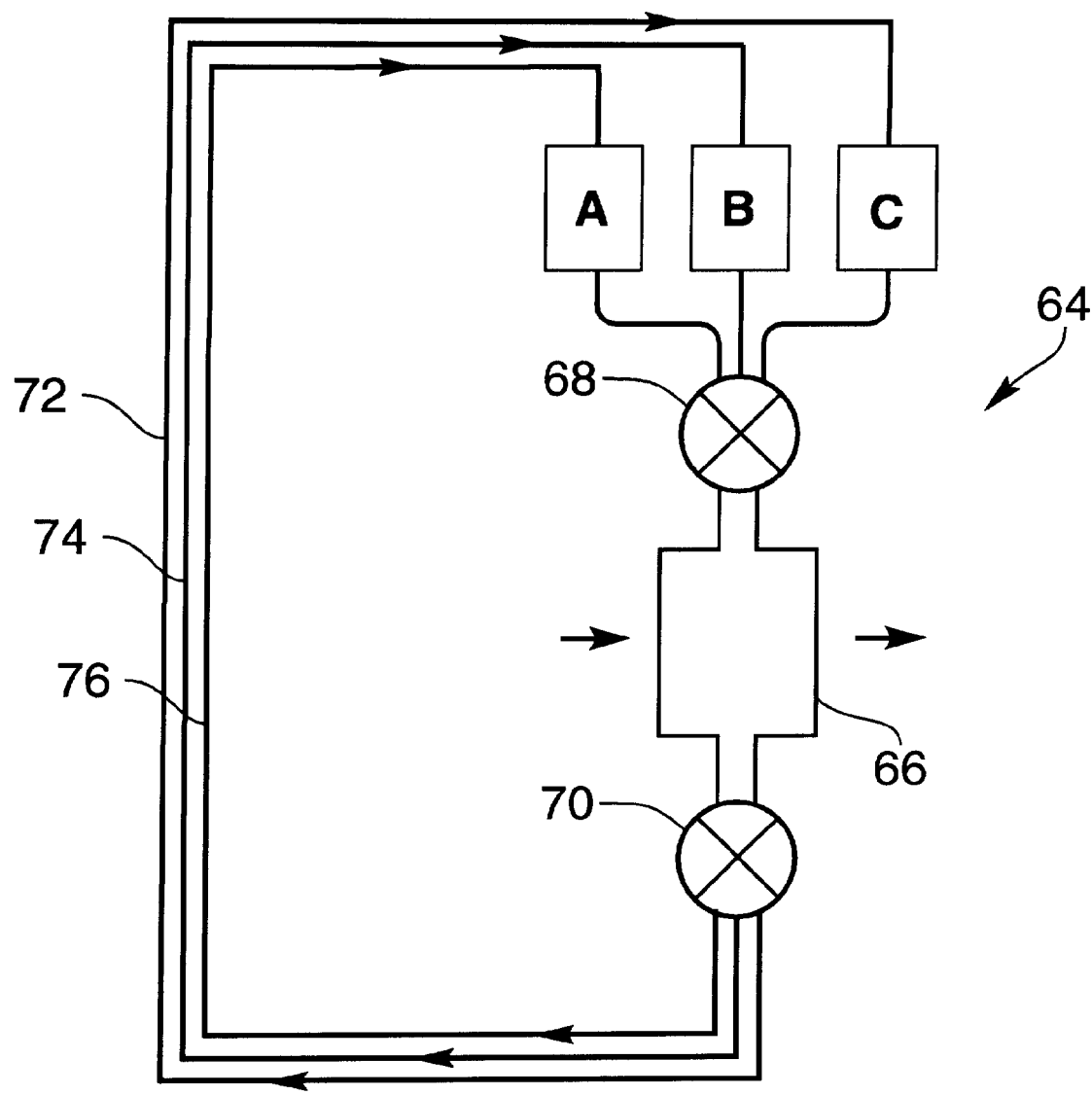
FIG. 5 is a schematic view of another alternative laser dye unit.

A further alternative embodiment of a laser dye unit 64 is shown in FIG. 5. Dye from one of the three dye cells A, B, and C is selectively delivered to a flow cell 66. Flow control valves 68 and 70 are selectively actuated to deliver dye from either of the cells A, B, and C. After use, the dye is returned to the cells through appropriate conduits 72, 74 and 76. Control of the valves, and circulating pumps (not shown) can be through the computer 50 of FIG. 2.

Figure 6:
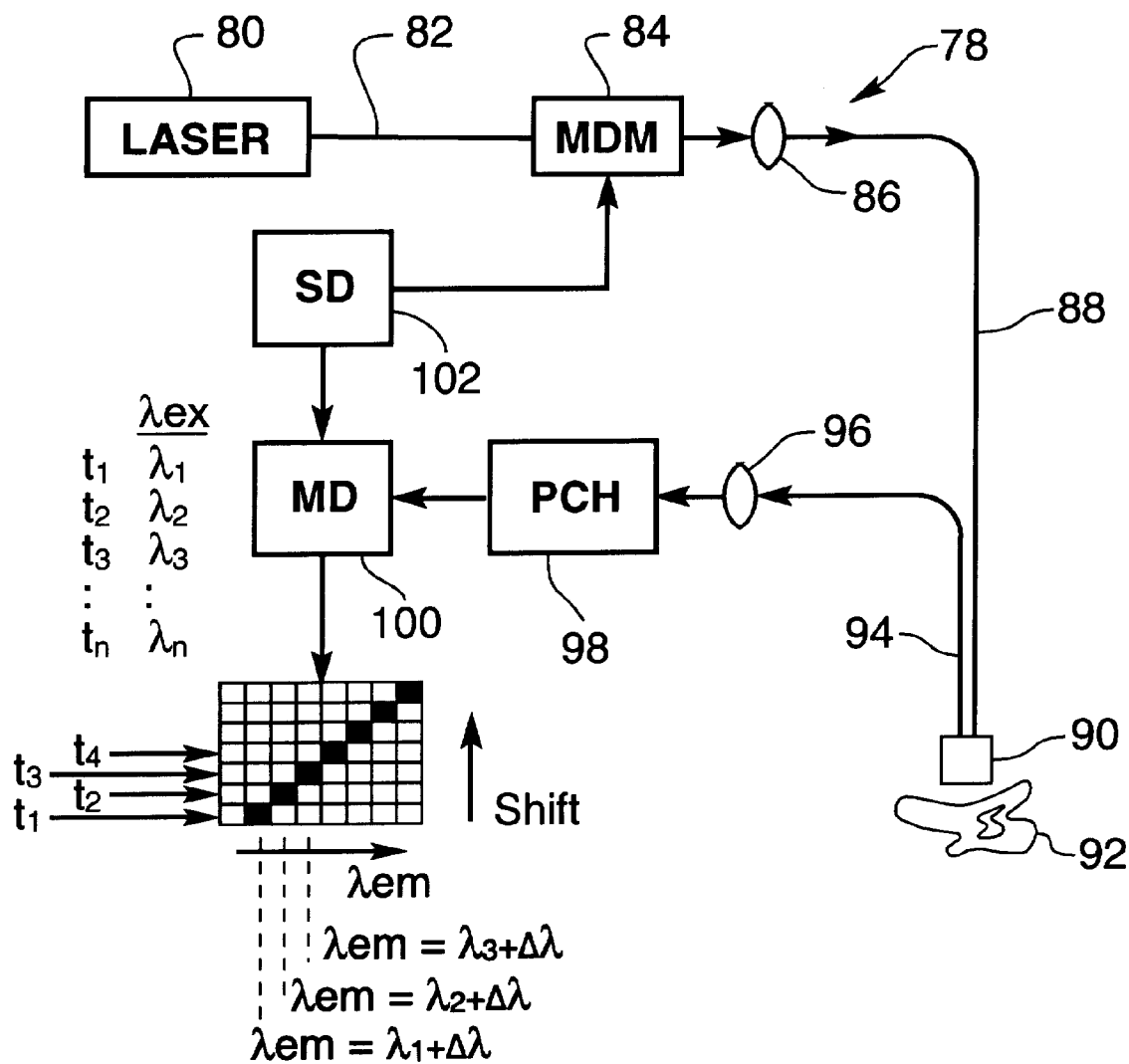
FIG. 6 is a schematic view of another preferred embodiment of an instrument for making chemical and biomedical identifications according to the present invention.

Another embodiment of an instrument 78 is illustrated in FIG. 6. The instrument 78 includes a laser source 80 which produces a pulsed beam 82. The beam 82 passes through a multiple dye module (MDM) 84. The scanning laser excitation radiation is delivered through focusing optics 86 and an optical fiber 88 to a probe 90 juxtaposed a sample 92.

Emission radiation is picked up by optical fiber 94 and delivered through focusing optics 96 to a polychromator (PCH) 98 and multichannel detector (MD) 100. The multichannel detector 100 can be a photodiode array, charge coupled device (CCD), or other similar devices.

A synchronizing device (SD) 102 synchronizes the scanning of $\lambda_{ex}$ with data acquisition of the multichannel detector. In this embodiment, the multichannel detector 100 produces a synchronous luminescence signal based on the black boxes shown in FIG. 6. This data can be collected by a personal computer which controls the synchronizing device 102 and displays and/or stores the synchronous luminescence signal. At each time, $t_n$, the excitation wavelength, $\lambda_n$ changes in a gradual progression. The synchronizing device 102 maintains a constant interval, $\Delta\lambda$, between the emission radiation and the excitation radiation. Note that the laser 22 and the MDM 26 of FIG. 2, or the laser 80 and the MDM 84 of FIG. 6 can be replaced by solid state scanning laser (e.g., titanium saphire laser) or other scanning laser systems equipped with optical parametric oscillator (OPO) devices.

Figure 7:
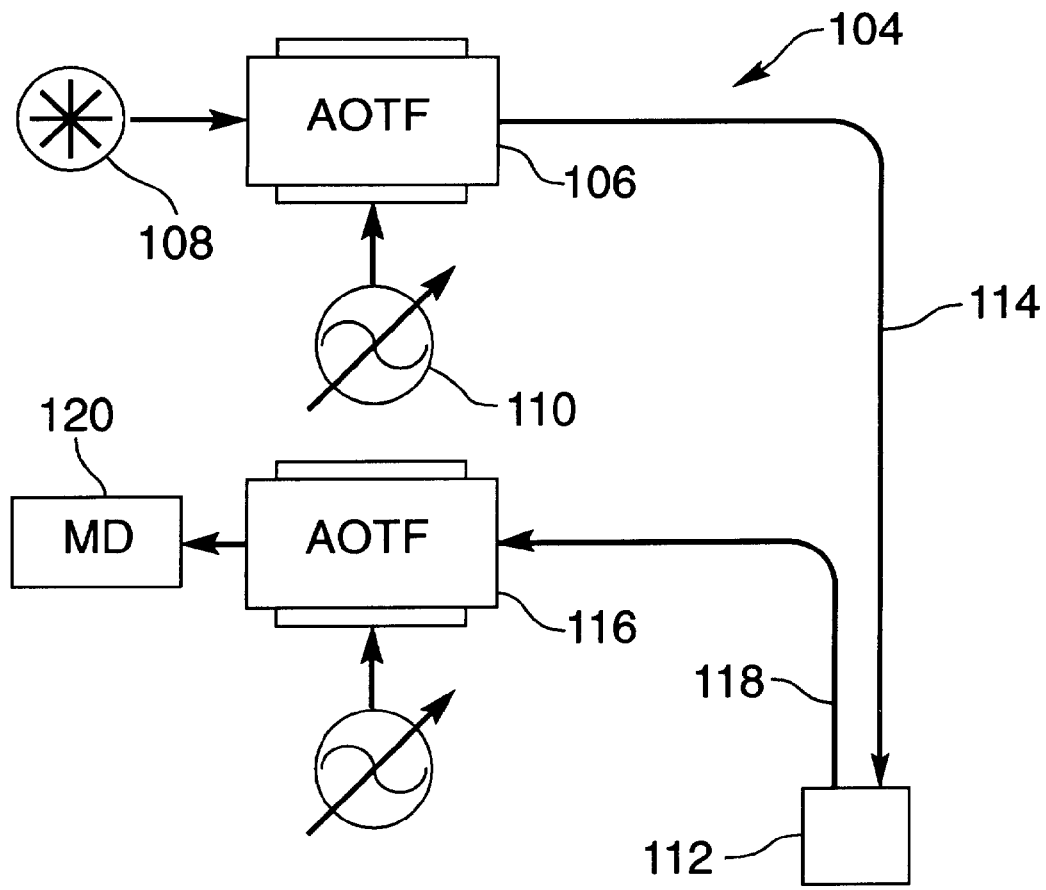
FIG. 7 is a schematic view of another preferred embodiment of an instrument for making chemical and biomedical identifications according to the present invention.

The instrument 104 shown in FIG. 7 uses an acousto-optic tunable filter (AOTF) 106 to scan the frequency of a light source 108. The light source 108 can be either a broad-band conventional light (e.g., xenon lamp) or a laser equipped with a dye module having a broad-band output (i.e., non scanning). The AOTF 106 is an electronically tunable spectral bandpass filter which can operate from the UV to the infrared regions of the optical spectrum. It operates via the interaction of light with a traveling acoustic wave through an anisotropic medium. An acoustic transducer is mounted on one end of a crystal, while an acoustic absorber is mounted on the other end. The transducer converts a high-frequency rf signal, from rf source 110, of a given frequency into a pressure wave which propagates laterally through the crystal at a given velocity $v_a$.

The acoustic absorber at the opposite end of the crystal serves to eliminate acoustic reflections which corrupt the primary acoustic waveform. The diffracted wavelengths are self-selected within the crystal to satisfy the momentum conservation between the incident $k_i$ and the diffracted $k_d$ photon wave vectors and the acoustic wave vector $k_a$ as follows:

$$k_d = k_i \pm k_a$$

One can achieve optical tuning by changing the rf frequency $f_a$ which is related to $\lambda$ as follows:

$$\lambda = v_a(n_e - n_o)a/f_a$$

where ne and no are the refractive indices of the extraordinary and ordinary wave, respectively, and a is a parameter depending upon the design of the AOTF.

The acoustic wave may be considered as the means for generating a transmission grating within the optical crystal. Instead of varying the angle of the incident beam, as would be the case for a normal diffraction grating in order to achieve wavelength selectivity, one varies the frequency of the electrical drive signal, allowing light of different wavelengths to be diffracted at the same angle. Hence with a fixed orientation of the crystal and the use of an rf generator, a tunable optical source is readily created from a broad-band source 108.

As seen in FIG. 7, the output of the AOTF 106 is the excitation radiation ($\lambda_{ex}$) which is delivered to a probe 112 through an optical fiber 114. Emission radiation ($\lambda_{em}$) is delivered to a second AOTF 116 through optical fiber 118. Two rf signals are generated for excitation ($\lambda_{ex}$) and emission ($\lambda_{em} = \lambda_{ex} + \Delta\lambda$) scanning. The output of the emission AOTF is delivered to a photodetector or a suitable multichannel detector (MD) 120, such as a CCD or PDA for spectral imaging.

Figure 8:
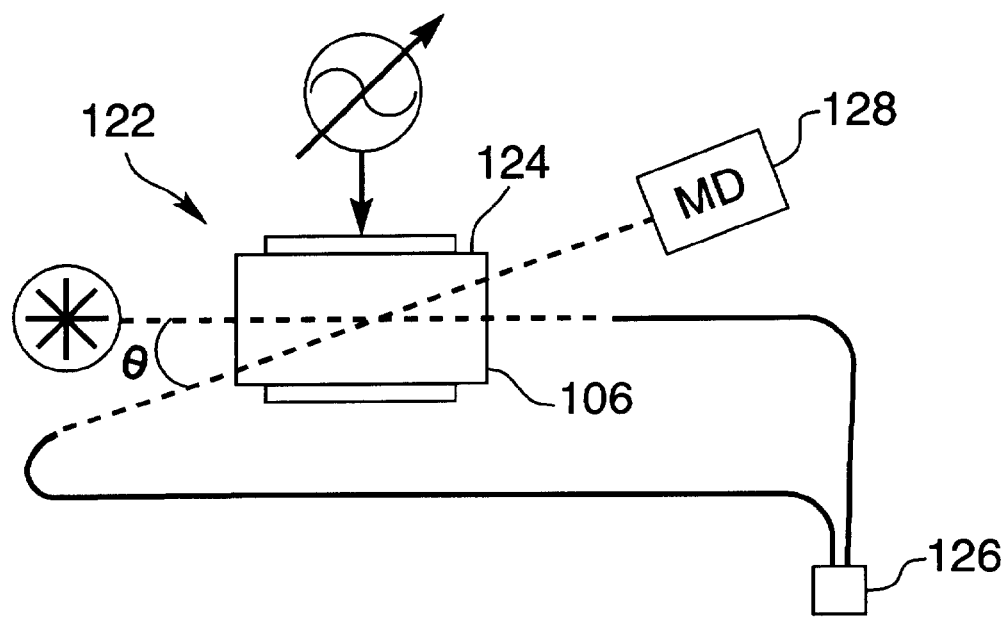
FIG. 8 is a schematic view of another preferred embodiment of an instrument for making chemical and biomedical identifications according to the present invention.

A variation of the FIG. 7 embodiment can be seen in FIG. 8, wherein an instrument 122 includes a single AOTF 124 provides means for scanning the frequency of the excitation radiation ($\lambda_{ex}$) delivered to a probe 126. Emission radiation ($\lambda_{em}$) is fed back through the AOTF 124 at an appropriate angle θ relative to the excitation path passing through the crystal of the AOTF 124. The crystal in the AOTF is made of TeO2, or other material of suitable properties. The angle θ is chosen so that $\lambda_{em} = \lambda_{ex} + \Delta\lambda$. Thus, in the embodiment of FIG. 8, the AOTF 124 is used both for excitation and emission. By selecting different angles of diffraction for emission and excitation, one can select $\lambda_1$ for excitation (related to $rf_1$) and $\lambda_1 + \Delta\lambda$ for emission using a different diffraction angle for emission. As in the FIG. 7 embodiment, a single-channel detector or a multichannel detector (MD) 128 is used to receive the emission signal.

Figure 9:
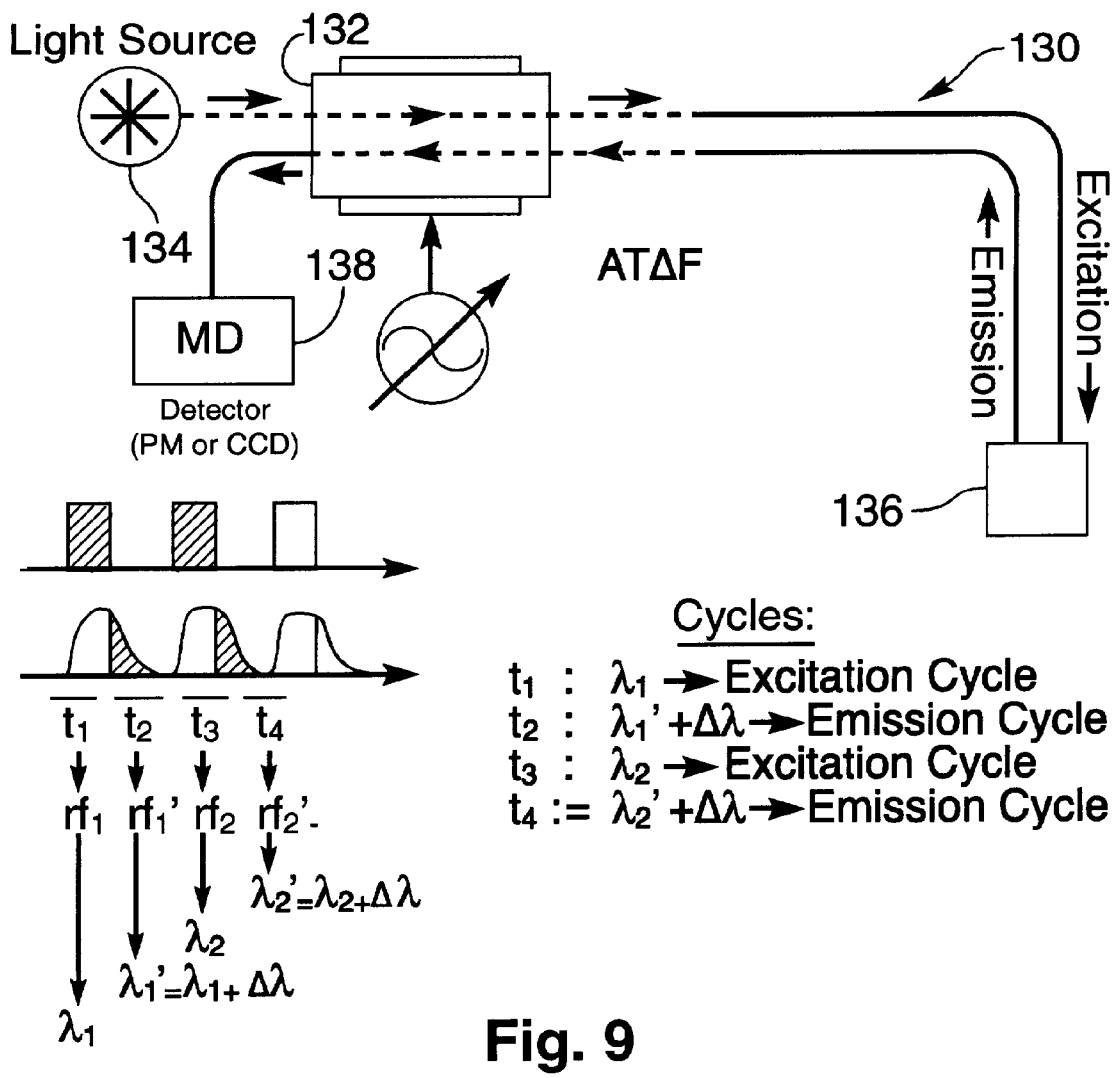
FIG. 9 is a schematic view of another preferred embodiment of an instrument for making chemical and biomedical identifications according to the present invention.

In the embodiment of FIG. 9, the instrument 130 also uses a single AOTF 132 which scans the wavelength of the light source 134. The rf source sends two rf signals alternately into the AOTF 132. By chopping and gated detection, the AOTF 132 can transmit excitation and emission radiation alternatively. As in the previous embodiments, a probe 136 can be juxtaposed any test sample of interest, and the emission radiation is detected with a multichannel detector 138, such as a CCD.

Figure 10:
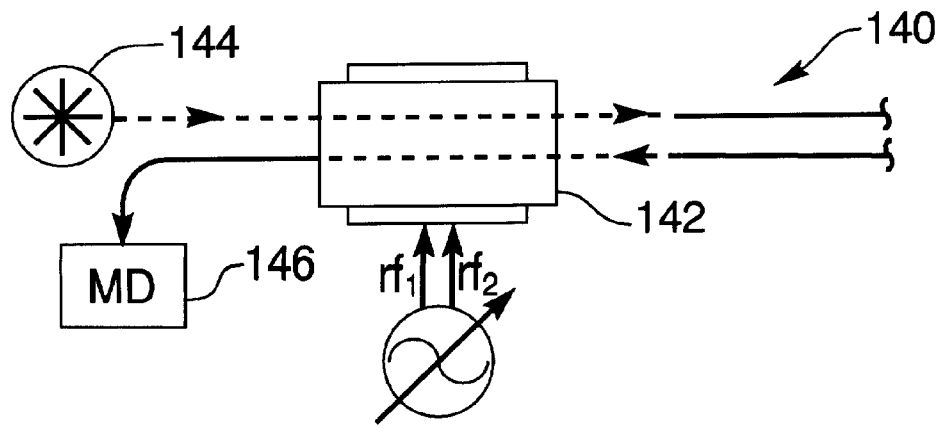
FIG. 10 is a schematic view of another preferred embodiment of an instrument for making chemical and biomedical identifications according to the present invention.

In the embodiment of FIG. 10, the instrument 140 uses a single AOTF 142 having a rf source which provides two simultaneous outputs rf1 and rf2. The rf1 signal produces an excitation radiation (λ1), and rf2 produces the emission radiation(λ2 =λ1 +Δλ). A light source 144 and MD 146 are provided as in the previous embodiments. The intensity of the diffracted beam is controlled by varying the amplitude or the amount of rf power applied to the crystal of the AOTF 142. This approach can also be used to rapidly modulate, or chop the filtered source for lock-in detection schemes.

Further variations of the AOTF embodiments include integration of the AOTF with a laser dye device, instead of gratings, for optical tuning. Also, AOTF devices can be integrated to multichannel detectors (PDA, CCD) instead of photomultipliers in order to detect two-dimensional SL imaging spectra, as in the FIG. 6 embodiment.

The present invention is effective in cancer tumor diagnostics. It offers more selectivity as compared with conventional fixed-excitation laser-induced fluorescence techniques. Subtle differences in spectral signatures of normal and cancer tissues can be detected more easily. The present invention combines the improved selectivity of synchronous scanning, the high intensity of laser excitation and the fast scanning of AOTF's.

The various embodiments described herein can be assembled from commercially available components. For example, and referring to FIG. 2, the laser 22 could be a small nitrogen/dye laser system available as models VSL-337 and VSL-DYE from Laser Science of Newton, Mass. (USA). The monochromator 38 used to collect fluorescence radiation can be a 10-cm focal length model H-10 monochromator made by ISA of Edison, N.J. (USA). The detector 42 can be a Hamamatsu Model R760 photomultiplier.

The pulse energy of the tunable laser output used in some experiments was 5–10 mJ/pulse over the range of wavelengths used in the experiments. The stepper motors used to drive both the dye module 26 and the monochromator 38 used digital (TTL) output pulses from an ADC card by MetraByte Corporation of Taunton, Mass. (USA), model DASH-16F. The same card was used for timing and to collect the analog signal. The signal from the photomultiplier 38 is preferably amplified with a fast preamplifier, such as a Stanford Research Systems Model SR445, DC-300 MHz, before being input to the boxcar integrator 44. The boxcar could be a Stanford Model SR250.

Figure 11:
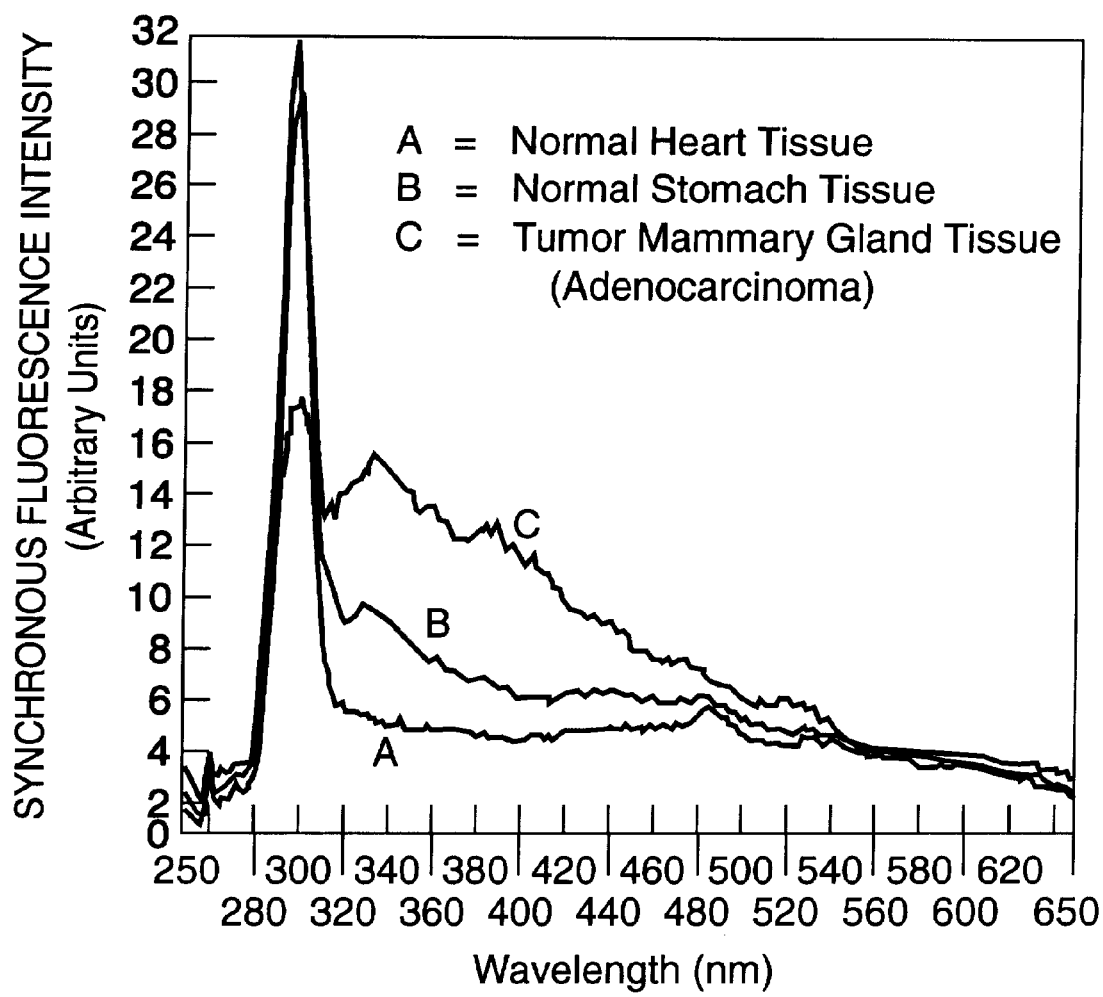
FIG. 11 is a display showing examples of synchronous luminescence of various types of tissues.

In experiments conducted using the FIG. 2 instrument, the scan speed was 10 nm/s. The laser repetition rate was 15 Hz and the time constant at the boxcar was 0.2 s (3 pulse average). After scans, all spectra were smoothed using a second-order Savitzky-Golay 37 point-smoothing algorithm. FIG. 11 is a display, as would be generated by a computer coupled to the instrument of the present invention, showing examples of synchronous luminescence spectra of various types of tissues. For the display of FIG. 11, a wavelength difference between excitation and emission of 10 nm was used.

The results displayed in FIG. 11 indicate that it is possible to use the different spectral profiles of the synchronous luminescence (SL) signal to characterize the tissues. Although the examples show results with tissue samples homogenized in solution, a similar measurement approach can also be used directly on tissue samples in vivo.

Normal and cancerous tissues can be better differentiated by the SL signals. It is expected that the techniques and instruments described herein can be applied to a wide variety of applications including, for example, diagnosis of skin, colon, stomach, cervical cancers, etc.

Figure 12:
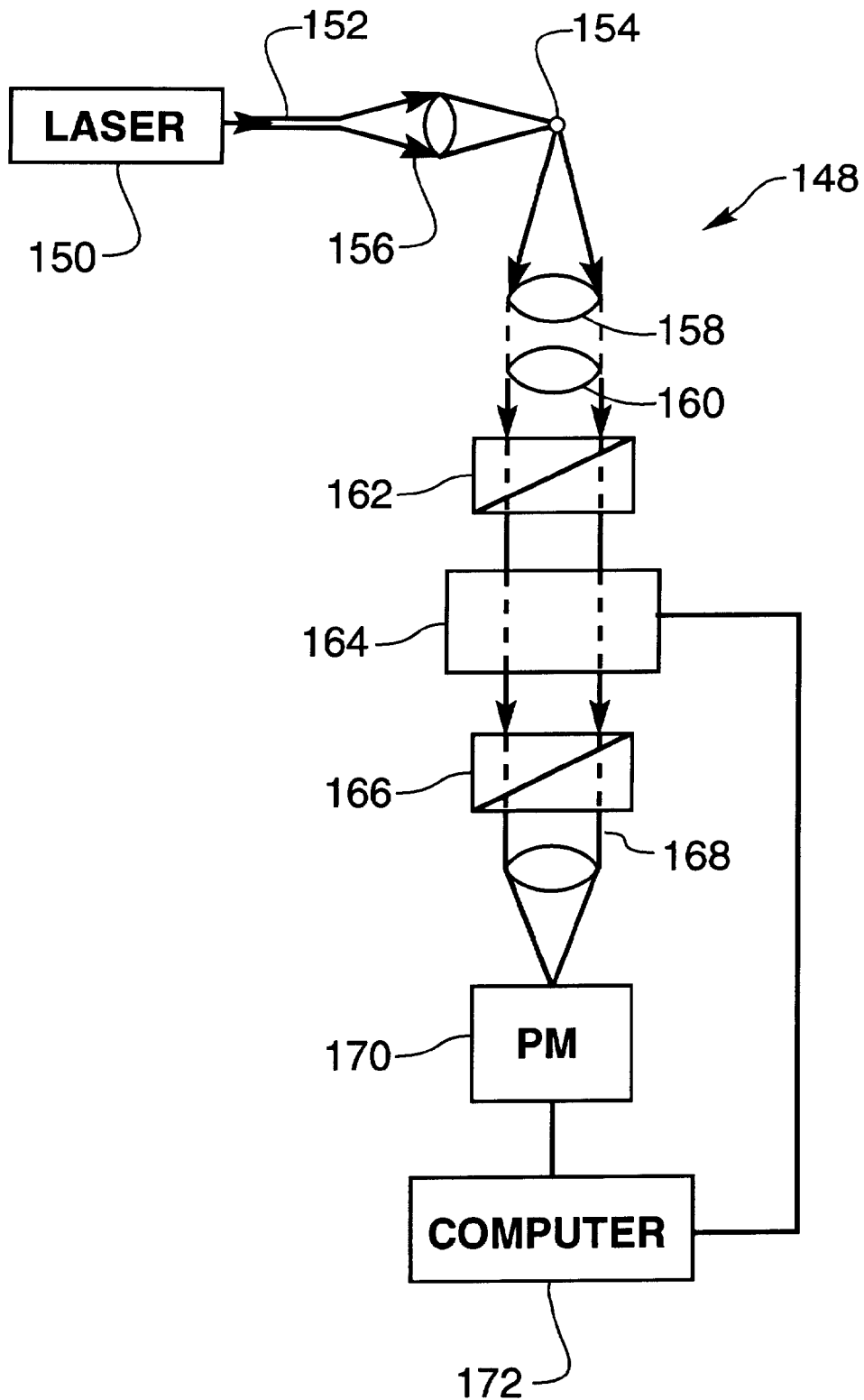
FIG. 12 is a schematic view of another preferred embodiment of an instrument for making chemical and biomedical identifications according to the present invention.

The AOTF embodiments described herein also can be assembled from commercially available components. In the embodiment of FIG. 12, the instrument 148 includes a helium-cadmium laser 150 (Omnichrome model 3074-6) whose output is directed to a silica clad-silica core optical fiber 152. The laser radiation emitted from the distal end of the optical fiber 152 is focused onto a sample 154, such as a quartz cuvette containing a sample solution, or a sample tissue) by a quartz lens 156.

The luminescence signal from the sample is collected at a right angle to the excitation beam. A pair of quartz lens 158 and 160 (f/4) are used to form a roughly collimated beam. A Glen-Taylor (polarizing) prism 162 allows only linearly polarized light into an AOTF 164 (Brimrose model QZAF-.25-.65). The polarization angle of the prism 162 is aligned with the polarization axis of the AOTF 164.

A second Glen-Taylor prism 166 is oriented orthogonally to the first prism 162, blocking the non-diffracted light. A quartz lens 168 focuses the filtered light onto a photomultiplier (PM) tube 170 (Hamamatsu model R928).

The AOTF 166 can have an operating spectral range of 250–650 nm. The spectral resolution is 0.9 nm and the diffraction efficiency is 25% at 400 nm. The radio frequency control signal applied to the AOTF is controlled by a DOS-based computer 172 using a 16-bit computer controller board.

The signal from the PM tube 170 is converted from analog to digital and then processed by the computer 172 which is programmed to control the AOTF for various scan modes. A real time data display mode can also be incorporated into the program.

Figure 13:
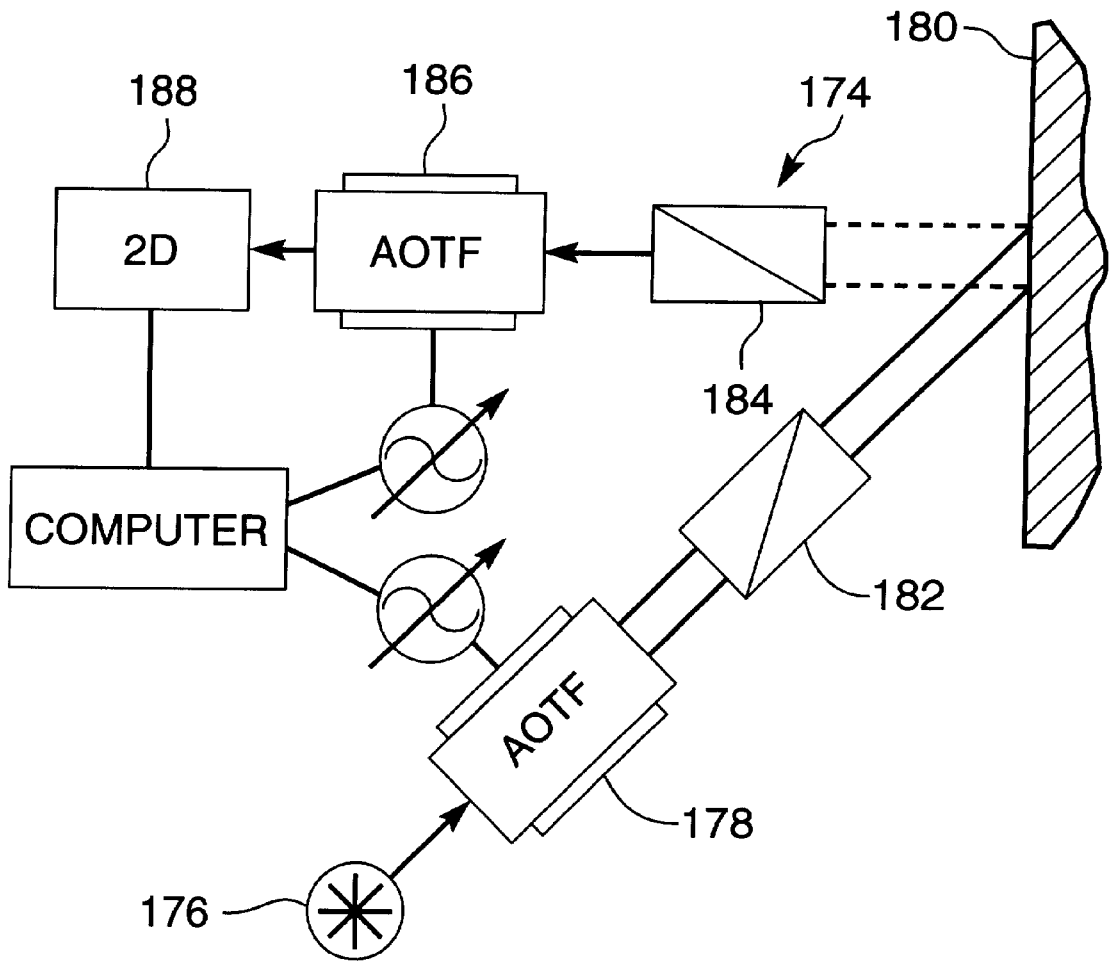
FIG. 13 is a schematic view of another preferred embodiment of an instrument for making chemical and biomedical identifications according to the present invention.

In FIG. 13 the laser is replaced by a broad-band light source equipped with a second AOTF. Both emission and excitation AOTFs can be scanned synchronously.

The use of an optical fiber in the embodiments using one or more AOTF's can be avoided. As shown in the embodiment of FIG. 13, the instrument 174 includes a light source 176 and excitation radiation AOTF 178. A surface 180 to be analyzed receives the scanning excitation radiation after passing through collimating optic 182. Emission radiation passes through collimating optic 184 and then to emission AOTF 186, and then to a two-dimensional detector (2D) 188. These signals are then converted into spectra by a computer 190, which also controls the scanning of the two AOTFs 178 and 186. Each point of the surface has a synchronous luminescence spectrum. In this embodiment, the light source is made to illuminate the area of interest, rather than a specific point. Thus, this type of instrument can be used to diagnose large areas of sample tissues since it allows the collection of the entire synchronous luminescence spectrum of every point on the area illuminated by the light source and under the field of view of the CCD detection system.

While no fiber optics were used in the FIG. 13 embodiment, a coherent bundle of fibers could be used to transmit individual pixels of images in the detection process.

Figure 14:
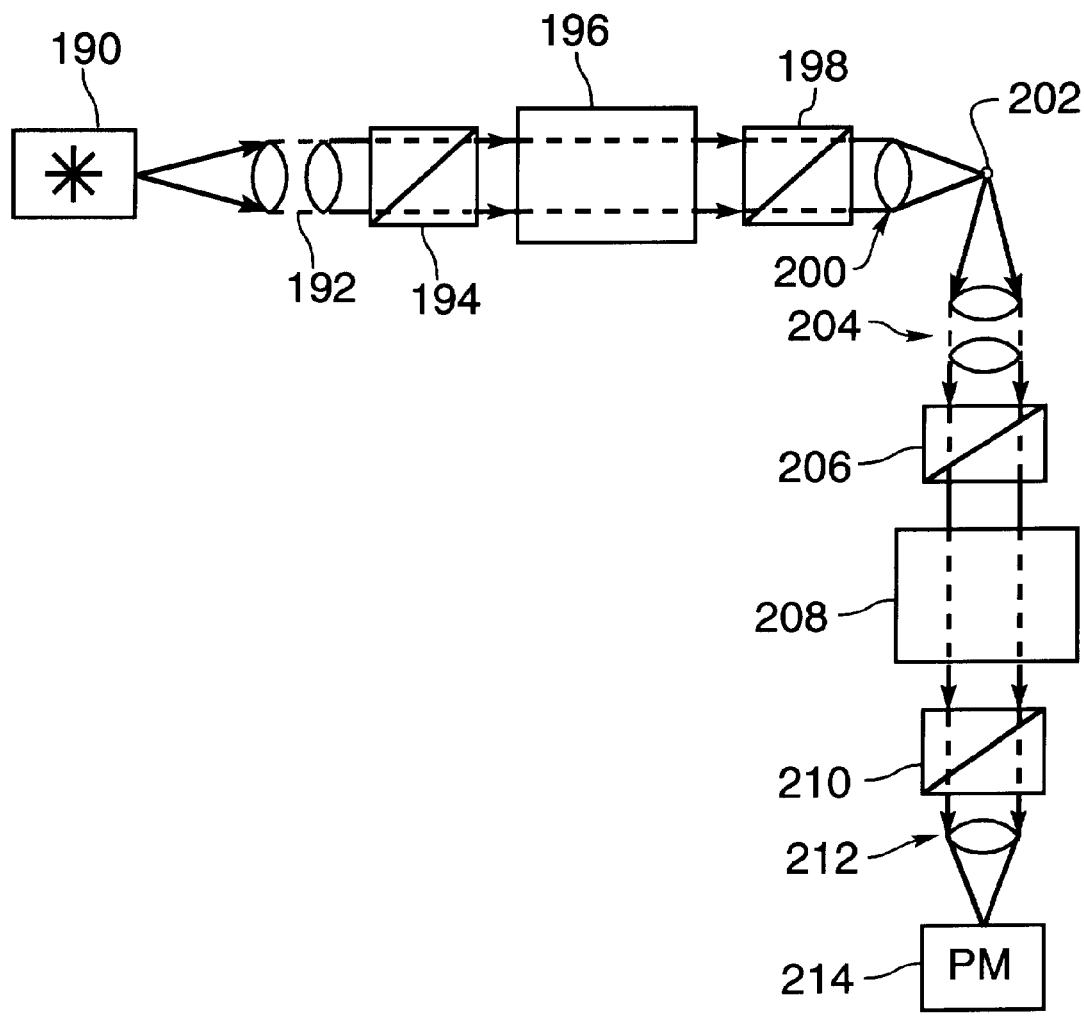
FIG. 14 is a schematic view of another preferred embodiment of an instrument for making chemical and biomedical identifications according to the present invention.

The embodiment of FIG. 14 includes a continuum light source 190, such as a high pressure xenon lamp. The lamp output passes through a pair of quartz lenses 192, which form a roughly collimated beam. A Glen-Taylor (polarizing) prism 194 is used to allow only linearly polarized light into an AOTF 196.

The output of the AOTF 196 passes through a second prism 198 and is focused by a lens 200 to a point 202 on a tissue sample. A second pair of quartz lenses 204 form a roughly collimated beam which passes through another polarizing prism 206. Emission radiation from the sample at point 202 is thus scanned by a second AOTF 208.

Prism 210 is oriented orthogonally relative to the prism 206 to block the non-diffracted light. A lens 212 is positioned to focus the filtered light onto a photomultiplier tube (PM) 214. Synchronous luminescence spectra can be produced and analyzed by coupling the output of the photomultiplier to a suitable analyzer, such as a personal computer with data acquisition capabilities.

Figure 15:
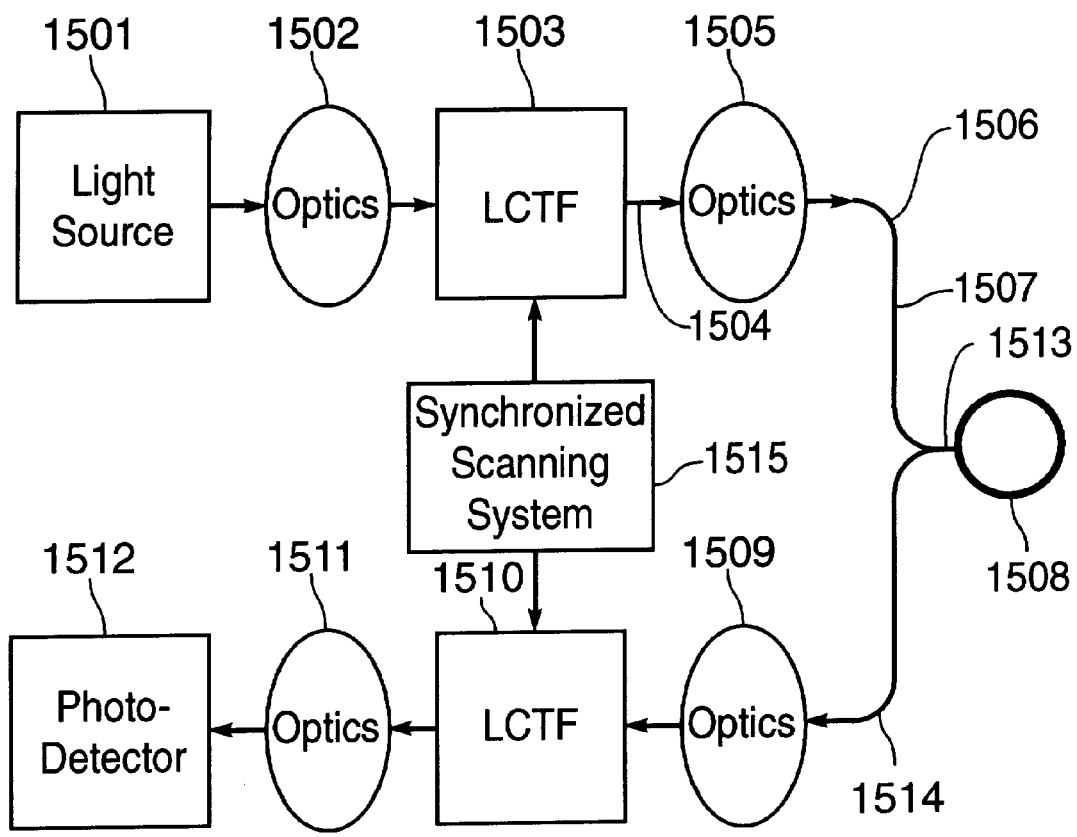
FIG. 15 is a schematic view of another preferred embodiment of an instrument for making chemical and biomedical identifications according to the present invention.

In the embodiment of FIG. 15, liquid crystal tunable filters (LCTF) are used. The LCTF involves birefringent filter systems, which utilize polarization control to transmit only a specific wavelength. Two classical designs for birefringent filters are the Lyot and the Solc designs (Evans, 1949 and 1958). Each design involves the use of birefringent optical elements to change the polarization of light between two polarizers. Such an assembly is often referred to as a stage of the filter. The input polarization is defined by the first polarizer of a stage. The polarization of this light is changed by birefringent waveplates, or retarders. The extent of polarization change depends on the wavelength of the light. The exit polarizer is used to attenuate the intensity of certain polarizations, therefore eliminating transmission of light of unwanted wavelengths.

Changing the value of each retarding element provides the tunability of birefringent filters. Mechanical methods for tuning (rotation of polarizers, mechanical adjustments of filter wave plates) are generally slow and not practical. An electro-optical method is to combine a liquid crystal with each fixed retarding element in the filter (Kopp, 1994). Nematic liquid crystals, used as solid state electro-optic retarders, can provide continuous spectral tunability on short time scales. The advances in LCTF technology provide an alternative system for rapid SL devices. Another alternative technology for wavelength scanning involve optical Fabry-Perot tunable filters (FPTF).

An embodiment of an SL system using LCTFs is shown in FIG. 15. The light from a broadband excitation light source 1501, such as a high-pressure Xenon lamp is passed through appropriate optics 1502, then through the excitation LCTF device 1503. The monochromatic light 1504 from the exit of the emission LCTF is focused by optics 1505 onto an end 1506 of a bifurcated optical fiber 1507 and transmitted to the sample 1508 for excitation. The luminescence emission of the sample is focused onto the optical fiber 1513 and transmitted through the bifurcated optical fiber 1514 onto optics 1509 to the emission LCTF device 1510. The light from emission LCTF 1510 is focused through optics 1511 onto photodetector 1512, which detects the light output from emission LCTF 1511.

Figure 15A:
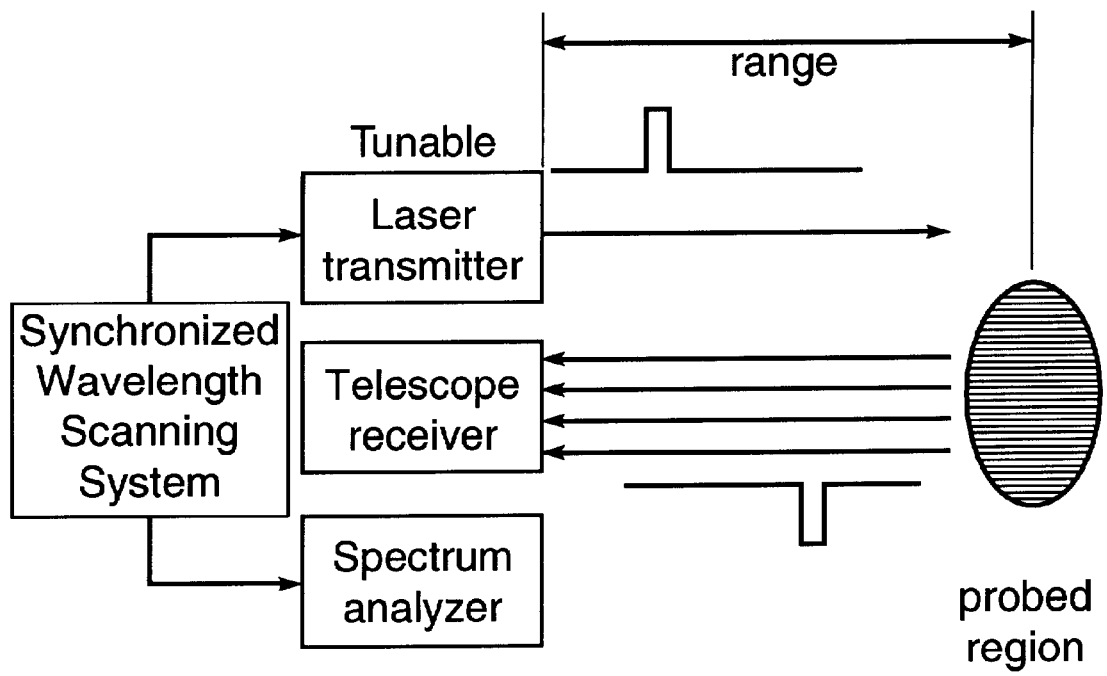
FIG. 15a is a schematic view of a monostatic SL-LIDAR system according to another embodiment of the present invention.
Figure 15B:
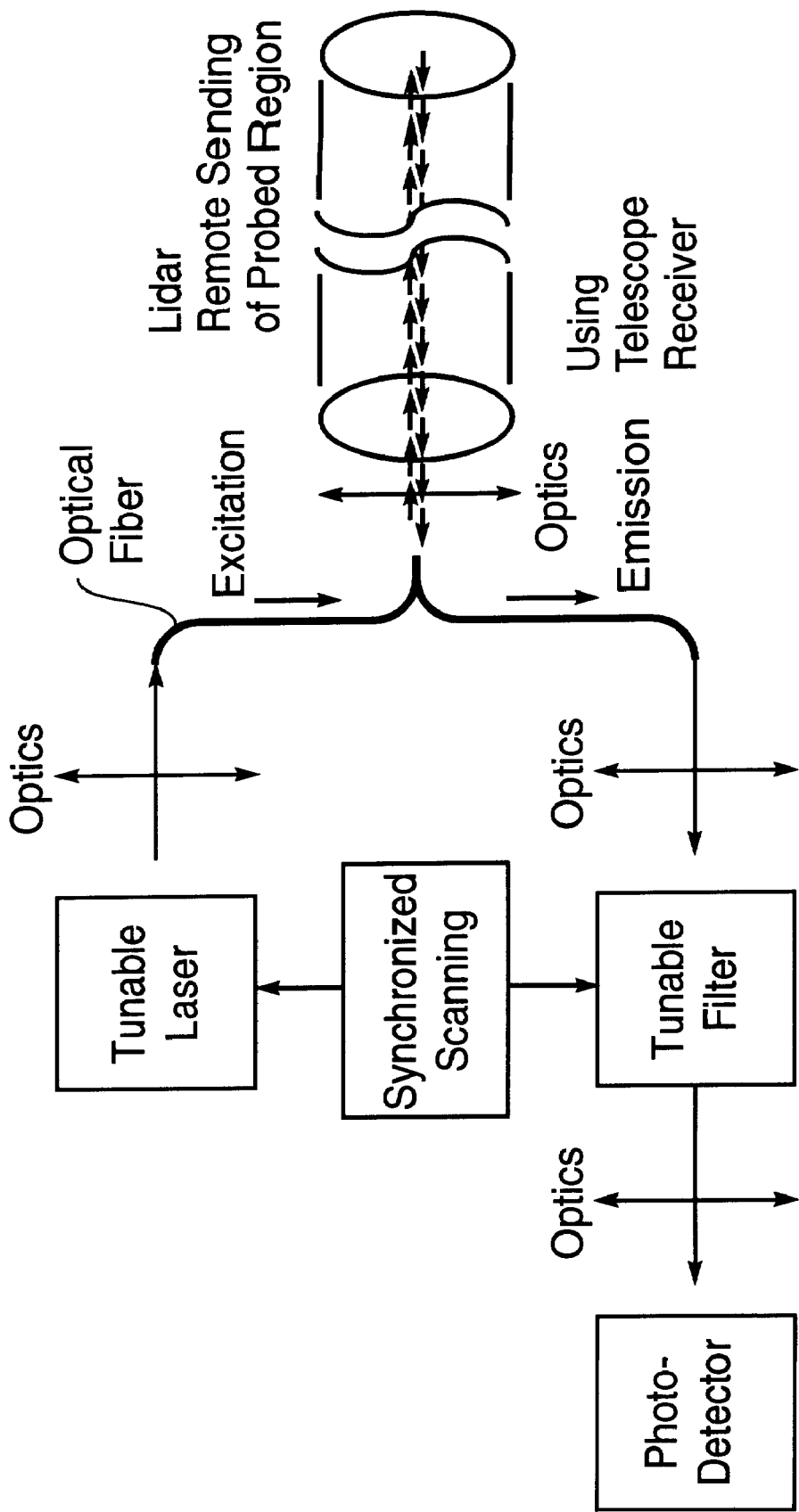

Currently, there is a great value in the ability to detect remotely the presence of chemical species or biological pathogens in the atmosphere when direct, personal examination is not possible. The SL device can be designed for remote probing of the atmosphere using LIDAR (light identification detection and ranging) method, which is based on the interaction of the laser excitation pulse with the chemical or biological species in the atmosphere along the path of the laser beam. Current LIDAR systems use fixed-wavelength laser excitation. An SL-LIDAR system enhances the selectivity of detection of LIDAR technology significantly. Most current LIDAR systems are monostatic—laser and receiver systems at the same location. Monostatic LIDAR systems rely on some mechanism of backscatter of laser light and detection of the back scattered radiation. The intensity of spectral composition of the radiation received through a telescope can be related to the characteristics of chemical and biological composition of the atmosphere. The general concept of a monostatic SL-LIDAR system is illustrated in FIG. 15A. A tunable pulsed laser is used for excitation. By monitoring the return SL signal as a function of time after the laser pulse, it is possible to map the species in the atmosphere along the laser beam as a function of distance from the SL-LIDAR system. By synchronously tuning the laser and detection wavelengths, it is possible to enhance the spectral selectivity significantly as compared with conventional LIDAR systems. A schematic diagram of an embodiment of an SL-LIDAR system is shown in FIG. 15B, and an example of its use in remote sensing is illustrated in FIG. 15C.

It is noteworthy that some LIDAR systems based on CW transmitter sources, often use a bistatic arrangement in order to provide spatial resolution by physically separating the transmitter and receiving systems. The spatial resolution is provided by the intersection of the source and the receiver's field of view. The SL-LIDAR concept is applicable to both monostatic and bistatic systems. Pulsed or CW tunable lasers may be used accordingly. Recently, tunable lasers equipped with optical parametric oscillators (OPO) can provide wide tuning ranges useful for SL-LIDAR applications. Tunable lasers equipped with OPO can also be used instead of lasers with dye modules as the excitation sources in all embodiments described.

Figure 16:
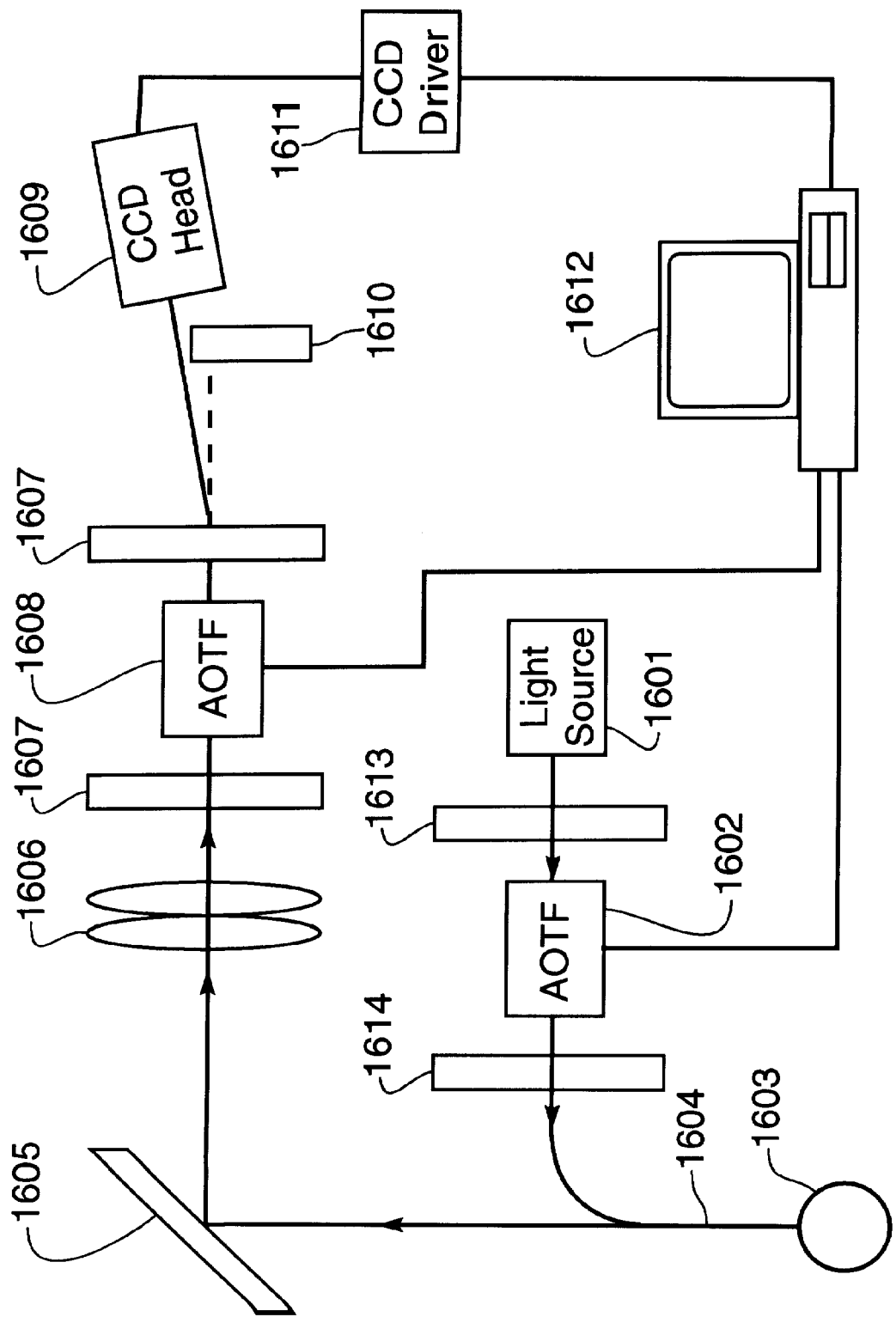
FIG. 16 is a schematic view of another preferred embodiment for imaging chemical and biomedical samples according to the present invention.

A major advantage of AOTFs and LCTFs and other types of tunable filters is their application to imaging. FIG. 16 is a block diagram of an imaging instrument using AOTFs. LCTFs or other tunable filters could be used instead of AOTFs, with the appropriate minor modifications to the control circuitry. The output from light source 1601 is filtered through excitation AOTF 1602, which is equipped with optical polarized 1613 and 1614 and applied to sample 1603 through bifurcated imaging fiber probe (IFP) 1604. The IPP may consist of bifurcated pairs of excitation and emission fibers arranged so the object image is conserved at the detector place. The light emitted from the output end of the imaging fiber probe (IFP) 1604 may be directed by mirror 1605 and is collected by an imaging lens 1606, filtered by emission AOTF 1608 equipped with optional polarizers 1607, and then imaged onto a charge-coupled device (CCD) head 1609. By changing the wavelength of the AOTFs, a spectrum can be acquired as a series of images (one for each wavelength). The TeO$_2$ AOTF can be purchased from Brimrose, Baltimore, Md. (model TEAF 10-45-7-S). The radio-frequency (rf) generator which controls the AOTF (not shown) (Brimrose-model AT) applies 0 to 25 W of rf power and is controlled by a DOS-based computer using a 16-bit computer controller board supplied by Brimrose. Software running on computer 1612 controls the AOTFs, supporting various scanning modes and fixed-frequency operation.

The CCD is a model ST-6 from Santa Barbara Instrument Group, Santa Barbara, Calif., based on a Texas Instruments TC241 CCD detector. The operating spectral range of such a system is from 330 to 1100 nm. The detector has an effective resolution of 375×242 pixels. Standard pixel size was 23×27 mm. A mechanical shutter is included in the optical head to facilitate taking dark frames. The CCD controller is based on the IBM 8088 microprocessor and runs at 8 kHz.

Note that the IFP is not required if the sample is easily accessible. The IFP is required when samples are located far from the device. An example of IFP can be purchased from Schott Fiber Optics Inc., South Bridge, Mass. It is an optical fiber image conduit for image transmission made of more than 400,000 individual 12 mm diameter fibers fused together, yielding a resolution twice that of the CCD. Individual fibers are made of glass translucent from 400 nm up to the IR region. Quartz fibers allow transmission in the ultraviolet range.

Figure 17A:
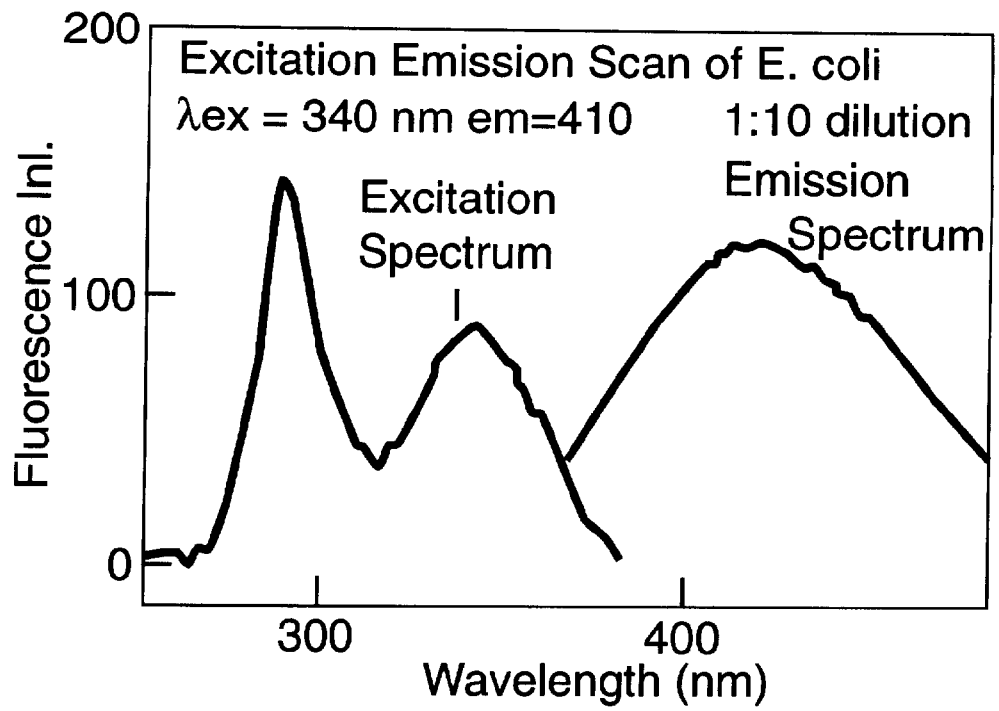
FIG. 17a is a display showing a fixed-excitation fluorescence emission spectrum (right curve) and a fixed-emission excitation spectrum (left curve) of E. Coli bacteria.
Figure 17B:
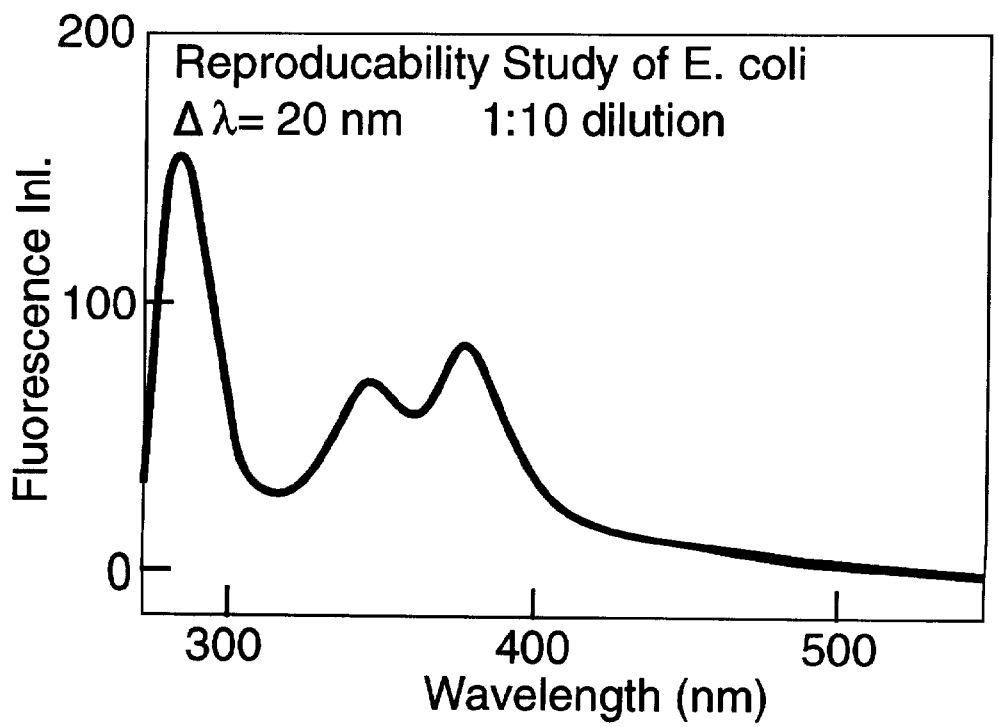
FIG. 17b is a display showing a synchronous luminescence spectrum of E. Coli bacteria.

The SL technique provides a drastic improvement in the of detection of a mixture of bacterial systems. For example, FIGS. 17a –b illustrate the basic effect of the SL technique in the detection of the *E. Coli* bacterial used as the sample model. The conventional fluorescence emission (using constant $\lambda_{ex}$=340 nm) and excitation (using constant $\lambda_{em}$=410 m) spectra of *E. Coli* are shown in FIG. 17a. The fixed-excitation fluorescence emission spectrum is a broad and featureless structure ranging from 320 nm to 600 nm. This spectral profile, which is characteristic of the fluorescent bacteria, remains unchanged when other excitation wavelengths are used. However, as shown in FIG. 17b, if the synchronous technique is applied using Δλ=20 nm, several resolved emission bands are observed and can be used for pathogen identification.

Figure 18A:
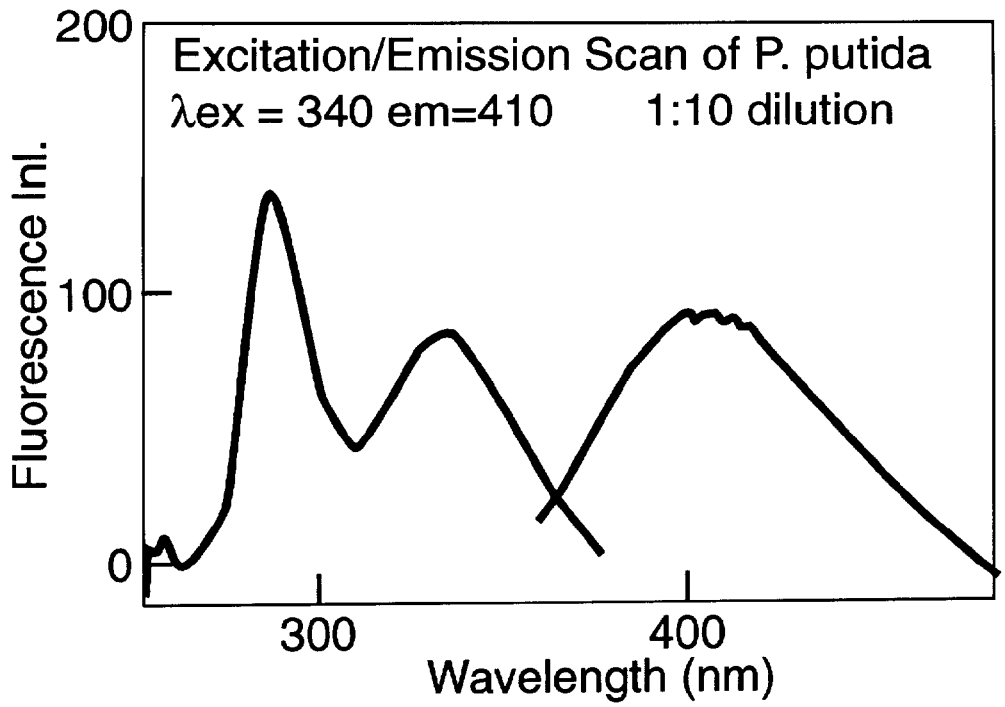
FIG. 18a is a display showing a fixed-excitation luminescence emission spectrum (right curve) and a fixed-emission excitation spectrum (left curve) of P. Putida bacteria.
Figure 18B:
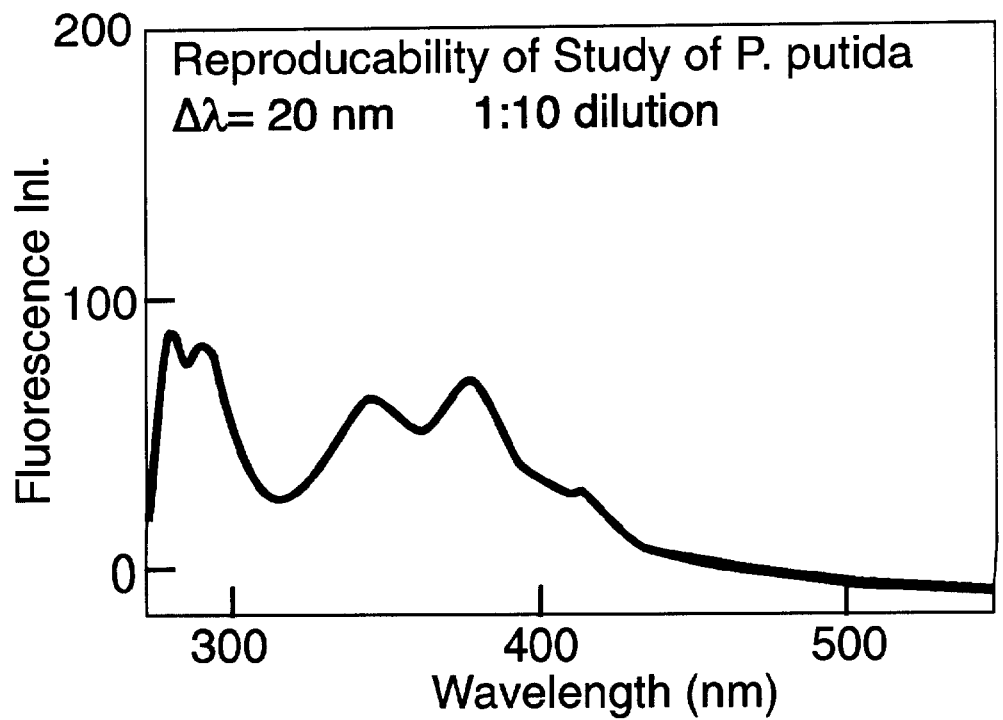
FIG. 18b is a display showing a synchronous luminescence spectrum of P. Putida bacteria.

*E. Coli* may be differentiated from other bacterial systems, such as, for example, *P. Putida* using the SL technique. FIG. 18a shows the fixed-emission and fixed excitation fluorescence spectra of the bacterial system *P. Putida*, whereas FIG. 18b shows the SL spectrum using Δλ=20 nm. It is difficult to distinguish *E. Coli* from *P. Putida* by comparing fixed-excitation spectra in FIGS. 17a and 18a, but the SL spectral signatures in FIGS. 17b and 18b clearly show the differences between the two bacterial systems.

In addition, further spectral selectivity can be achieved by using second derivative spectra, as shown in FIG. 19.

The present invention may be used to test a wide variety of samples for biological pathogens. For example, tissue samples, either in vitro or in vivo, may be tested to detect and identify infectious agents. Food samples may be tested to detect and identify biological pathogens, such as, for example, *E. Coli* and other organisms. The present invention is useful to perform environmental monitoring, such as bacterial identification in water supplies and bioremediation. Likewise, the present invention is useful in the field of biotechnology, to detect and identify bacteria in bioprocesses. Also, the present invention is useful in the detection of biological warfare agents in solid, liquid and air samples. Moreover, the present invention is useful in the detection of infectious agents, for example, infectious pathogens.

While advantageous embodiments have been chosen to illustrate the invention, it will be understood by those skilled in the art that various changes and modifications can be made therein without departing from the scope of the invention as defined in the appended claims.

What is claimed is:

1. A method of testing a sample comprising the steps of:
   exposing the sample to an excitation radiation and thereby generating an emission radiation;
   synchronously scanning the wavelength of the excitation radiation and the wavelength of the emission radiation to produce a spectrum; and
   correlating the spectrum to an infectious agent in the sample.

2. The method according to claim 1, wherein the exposing step comprises directing an output beam from a laser light source to the sample through at least one optical fiber.

3. The method according to claim 2, wherein the sample is a tissue sample.

4. The method according to claim 3, further comprising directing the output of the laser light source into a probe disposed in vivo next to the tissue sample.

5. The method according to claim 2, wherein the scanning step further comprises directing the output beam of the laser source through a dye module having a plurality of dyes, and changing the dyes to achieve a range of excitation wavelengths.

6. The method according to claim 2, wherein the scanning step further comprises directing the output beam of the laser source through a dye container, and selectively moving a plurality of dyes into the dye container to achieve a range of excitation wavelengths.

7. The method of claim 2, wherein the excitation scanning step further comprises directing the output beam of the laser source through an optical parametric oscillator to achieve a range of excitation wavelengths.

8. The method according to claim 1, wherein the synchronously scanning step comprises maintaining a constant interval between the wavelength of the excitation radiation and the emission radiation during synchronous scanning.

9. The method according to claim 8, wherein the exposing step comprises directing a laser beam to an air sample and detecting a backscattered signal remotely.

10. The method according to claim 1, wherein the synchronous scanning step comprises directing the excitation radiation into a first acousto-optic tunable filter, and changing an input radio frequency of the first filter to achieve a range of excitation wavelengths.

11. The method according to claim 10, wherein the synchronous scanning step further comprises directing the emission radiation into a second acousto-optic tunable filter, and changing an input radio frequency of the second filter to achieve a range of emission wavelengths.

12. The method according to claim 10, wherein the synchronous scanning step further comprises directing the emission radiation into the first filter at an angle relative to the excitation radiation.

13. The method according to claim 10, wherein the synchronous scanning step further comprises directing the emission radiation into the first filter, alternately providing two radio frequency signals to the first filter to alternately pass the excitation and emission radiations through the first filter, and alternately detecting the emission radiation when the first filter is not transmitting the excitation radiation.

14. The method according to claim 1, wherein the synchronous scanning step comprises directing the excitation radiation into a first liquid crystal tunable filter, and adjusting a retarding element of the first filter to achieve a range of excitation wavelengths.

15. The method according to claim 14, wherein the synchronous scanning step further comprises directing the emission radiation into a second liquid crystal tunable filter, and adjusting a retarding element of the second filter to achieve a range of emission wavelengths.

16. The method according to claim 1, wherein the exposing step comprises directing a laser beam to an air sample and detecting a backscattered signal remotely.

17. The method of claim 1, wherein the sample is a food product.

18. The method of claim 1, comprising the step of correlating the spectrum to an infectious pathogen.

19. An apparatus for testing a sample comprising:
   means for exposing the sample to an excitation radiation and thereby generating an emission radiation;
   means for synchronously scanning the wavelength of the excitation radiation and the wavelength of the emission radiation to produce a spectrum; and
   means for correlating the spectrum to an infectious agent in the sample.

20. An apparatus according to claim 19, wherein the exposing means comprises a laser outputting a beam and the synchronous scanning means includes a multiple dye module having a plurality of dyes, each capable of changing the wavelength of the laser beam within a specified range.

21. An apparatus according to claim 19, wherein the exposing means comprises a laser outputting a beam and the synchronous scanning means includes means for maintaining a constant interval between the wavelength of the excitation radiation and the emission radiation during synchronous scanning.

22. An apparatus according to claim 19, wherein the exposing means comprises a laser source outputting a beam, and the scanning means comprises means for directing the output beam of the laser source through a dye module having a plurality of dyes, and means for changing the dyes to achieve a range of excitation wavelengths.

23. An apparatus according to claim 19, wherein the exposing means comprises a light source and the scanning means includes a first acousto-optic tunable filter having a variable input radio frequency selected to achieve a range of excitation wavelengths.

24. An apparatus according to claim 23, wherein the synchronous scanning means further comprises a second acousto-optic tunable filter having a variable input radio frequency selected to achieve a range of emission wavelengths.

25. An apparatus according to claim 19, wherein the exposing means comprises a light source and the scanning means comprises a first liquid crystal tunable filter having an adjustable retarding element selected to achieve a range of excitation wavelengths.

26. The apparatus according to claim 25, wherein the synchronous scanning means further comprises a second liquid crystal tunable filter having an adjustable retarding element selected to achieve a range of emission wavelengths.

27. The apparatus of claim 19, wherein said infectious agent is an infectious pathogen.

28. A method of imaging a sample comprising the steps of:
   exposing the sample to an excitation radiation and thereby generating an emission radiation;
   synchronously scanning the wavelength of the excitation radiation and the wavelength of the emission radiation to produce an imaged spectrum; and
   correlating the imaged spectrum to an infectious agent in the sample.

29. The method according to claim 28, wherein the sample is a tissue sample.

30. The method according to claim 29, further comprising the step of directing an output of a laser light source into a probe disposed in vivo next to the tissue sample.

31. The method according to claim 29, further comprising the step of:
   correlating the imaged spectrum to a condition of the tissue sample.

32. The method according to claim 28, wherein the exposing step comprises directing an output beam from a laser light source to the sample through at least one optical fiber.

33. The method according to claim 28, wherein the synchronously scanning step comprises maintaining a constant interval between the wavelength of the excitation radiation and the emission radiation during the synchronous scanning.

34. The method according to claim 28, wherein the scanning step further comprises directing an output beam of a laser source through a dye module having a plurality of dyes, and changing the dyes to achieve a range of excitation wavelengths.

35. The method according to claim 28, wherein the scanning step further comprises directing an output beam of a laser source through a dye container, and selectively moving a plurality of dyes into the dye container to achieve a range of excitation wavelengths.

36. The method according to claim 28, wherein the synchronous scanning step comprises directing the excitation radiation into a first acousto-optic tunable filter, and changing an input radio frequency of the first filter to achieve a range of excitation wavelengths.

37. The method according to claim 36, wherein the synchronous scanning step further comprises directing the emission radiation into a second acousto-optic tunable filter, and changing an input radio frequency of the second filter to achieve a range of emission wavelengths.

38. The method according to claim 36, wherein the synchronous scanning step further comprises directing the emission radiation into the first filter at an angle relative to the excitation radiation.

39. The method according to claim 36, wherein the synchronous scanning step further comprises directing the emission radiation into the first filter, alternately providing two radio frequency signals to the first filter to alternately pass the excitation and emission radiations through the first filter, and alternately detecting the emission radiation when the first filter is not transmitting the excitation radiation.

40. The method according to claim 28, wherein the synchronous scanning step comprises directing the excitation radiation into a first liquid crystal tunable filter, and adjusting a retarding element of the first filter to achieve a range of excitation wavelengths.

41. The method according to claim 28, wherein the synchronous scanning step further comprises directing the emission radiation into a second liquid crystal tunable filter, and adjusting a retarding element of the second filter to achieve a range of emission wavelengths.

42. The method of claim 28, comprising the step of correlating the imaged spectrum to an infectious pathogen.

43. An apparatus for imaging a sample comprising:
   means for exposing the sample to an excitation radiation and thereby generating an emission radiation; and
   means for synchronously scanning the wavelength of the excitation radiation and the wavelength of the emission radiation to produce an imaged spectrum; and
   correlating the imaged spectrum to an infectious agent in the sample.

44. The apparatus according to claim 43, wherein the sample is a tissue sample.

45. The apparatus according to claim 44, further comprising means for:
   correlating the imaged spectrum to a condition of the tissue sample.

46. The apparatus according to claim 44, further comprising means for:
   correlating the imaged spectrum to a biological pathogen in the tissue sample.

47. The apparatus according to claim 44, further comprising a probe positionable in vivo next to the tissue sample, an output of a laser light source being directable into the tissue sample through the probe.

48. An apparatus according to claim 43, wherein the exposing means comprises a light source and the scanning means includes a first acousto-optic tunable filter having a variable input radio frequency selected to achieve a range of excitation wavelengths.

49. An apparatus according to claim 48, wherein the synchronous scanning means further comprises a second acousto-optic tunable filter having a variable input radio frequency selected to achieve a range of emission wavelengths.

50. An apparatus according to claim 43, wherein the exposing means comprises a light source and the scanning means comprises a first liquid crystal tunable filter having an adjustable retarding element selected to achieve a range of excitation wavelengths.

51. The method according to claim 50, wherein the synchronous scanning means further comprises a second liquid crystal tunable filter having an adjustable retarding element selected to achieve a range of emission wavelengths.

52. The apparatus of claim 43, wherein said infectious agent is an infectious pathogen.

* * * * *